United States Patent
Tatarintsev et al.

(12) 
(10) Patent No.: US 6,177,475 B1
(45) Date of Patent: *Jan. 23, 2001

(54) METHODS OF USING INTEGRIN MODULATORS FOR TREATMENT OF INFLAMMATION

(75) Inventors: Alexander V. Tatarintsev; Ali S. Turgiev, both of Moscow (RU); John B. Davidson, Chicago, IL (US)

(73) Assignee: Billings Pharmaceuticals, Inc., Chicago, IL (US)

(*) Notice: Under 35 U.S.C. 154(b), the term of this patent shall be extended for 0 days.

This patent is subject to a terminal disclaimer.

(21) Appl. No.: 08/854,466

(22) Filed: May 12, 1997

Related U.S. Application Data

(63) Continuation-in-part of application No. PCT/US97/00583, filed on Jan. 13, 1997, which is a continuation-in-part of application No. 08/698,893, filed on Aug. 16, 1996, now abandoned, which is a continuation-in-part of application No. 08/585,190, filed on Jan. 11, 1996, now Pat. No. 5,948,821, which is a continuation-in-part of application No. 08/445,146, filed on May 19, 1995, now abandoned, which is a continuation-in-part of application No. 07/906,850, filed on Jun. 30, 1992, now abandoned.

(51) Int. Cl.$^7$ .................. A61K 31/105; A61K 31/095
(52) U.S. Cl. ............................... 514/707; 514/706
(58) Field of Search .................... 514/707, 706

(56) References Cited

U.S. PATENT DOCUMENTS

| | | | |
|---|---|---|---|
| 4,126,676 | 11/1978 | Sanders | 424/98 |
| 4,341,762 | 7/1982 | Haast | 424/88 |
| 4,643,994 | 2/1987 | Block et al. | |
| 4,665,088 | 5/1987 | Apitz-Castro et al. | |
| 4,876,281 | 10/1989 | Yoshida et al. | 514/517 |
| 5,066,658 | 11/1991 | Demers et al. | 514/707 |
| 5,093,122 | 3/1992 | Kodera | 424/195.1 |
| 5,380,646 | 1/1995 | Knight et al. | 424/1.69 |
| 5,464,855 | 11/1995 | Capiris et al. | 514/382 |
| 5,731,288 | * 3/1998 | Markland, Jr. et al. | |
| 5,856,363 | 1/1999 | Tatarintsev et al. | |
| 5,863,954 | 1/1999 | Tatarintsev et al. | |
| 5,863,955 | 1/1999 | Tatarintsev et al. | |
| 5,932,621 | 8/1999 | Tatarintsev | |

FOREIGN PATENT DOCUMENTS

| | | |
|---|---|---|
| 153881 | 9/1985 | (EP). |
| 185324 | 6/1986 | (EP). |
| WO 94/15953 | 7/1994 | (WO). |

OTHER PUBLICATIONS

Sud'ina et al., 1991, *Biochimica et Biophysica Acta*, 1091:257–60.

Tatarintsev et al., International Conference on Molec. Biol. Aspects of Diagnostics and Therapy of AIDS, Conference poster and abstract, Jul. 2–5, 1991.

Tatarintsev et al., European Developmental Biology Congress, Conference abstract, Aug. 11–15, 1991.

Tatarintsev et al., Keystone Symposia on Molec. & Cell. Biol., Conference abstract, Feb. 1992.

Tatarintsev et al., Keystone Symposia on Molec. & Cell. Biol., Conference abstract, Mar. 1992.

Karamov et al., Keystone Symposia on Molec. & Cell. Biol., Conference abstract, Apr. 4, 1992.

(List continued on next page.)

*Primary Examiner*—William R. A. Jarvis
(74) *Attorney, Agent, or Firm*—Sheridan Ross P.C.

(57) ABSTRACT

The invention provides methods of treating inflammatory diseases and conditions by administering an effective amount of an integrin modulating agent, as further defined and specified herein, to an animal suffering from one of the diseases or conditions. The preferred integrin modulating agents are ajoene and disintegrins, variants and analogs of disintegrins.

14 Claims, 1 Drawing Sheet

OTHER PUBLICATIONS

Tatarintsev et al., Keystone Symposia on Molec. & Cell. Biol., Conference abstract, Apr. 4, 1992.
Tatarintsev et al., VII Int'l Conf. on AIDS, Conference abstract, Jul. 19–24, 1992.
Apitz–Castro et al., 1983, *Thrombosis Research*, 32(2):155–69.
Block et al., 1984, *J. Am. Chem. Soc.*, 106(26):8295–96.
Block et al., 1986, *J. Am. Chem. Soc.*, 108(22):7045–55.
Apitz–Castro et al., 1986, *Thrombosis Research*, 42:303–11.
Apitz–Castro et al., 1986, *Biochemical and Biophysical Research Communications*, 141(1):145–50.
Jain et al., 1987, *TIBS*, 12(7):252–54.
Jamaluddin et al., 1988, *Biochemical and Biophysical Research Communications*, 153(1):479–86.
Apitz–Castro et al., 1988, *Drug Research*, 38(7):901–04.
Debouzy et al., 1989, *European Biophysics Journal*, 17:211–16.
Rendu et al., 1989, *Biochemical Pharmacology*, 38(8):1321–28.
Apitz–Castro et al., 1991, *Biochemica et Biophysica Acta*, 1094(3):269–80.
Apitz–Castro et al., 1991, *Thrombosis and Haemotology*, 65(6):Abstract No. 1380 at p. 1079.
Apitz–Castro et al., 1991, *Thrombosis and Haemotology*, 65(6):Abstract No. 1603 at p. 1141.
Srivestava, 4th Erfurt Conference on Platelets, Jun. 22–27, 1992, p. 19.
Ali et al., Book of Abstracts, VIII Int'l Conf. on Prostaglandins & Related Compounds, Montreal, Jul. 1992, abstract No. 54.
Belman et al., 1989, *Journal of Biochemical Toxicology*, 4(3):151–60.
Scharfenberg et al., 1990, *Cancer Letters*, 53:103–08.
Yoshida et al., 1987, *Applied and Environmental Microbiology*, 53(3):615–17.
San–Blas et al., 1989, *Antimicrobial Agents and Chemotherapy*, 33(9):1641–44.
Singh et al., 1990, *Can J. Bot.*, 68(6):1354–56.
Gargouri et al., 1989, *Biochemica et Biophysica Acta*, 1006(1):137–39.
Mohammed et al., 1986, *Thrombosis Research*, 44:793–806.
Mayeux et al., 1986, *Prostaglandins*, 1, 45(3): Abstract 2936 at p. 660.
Mayeux et al., 1988, *Agents and Actions*, 25:182–90.
Mirelman et al., 1987, *The Journal of Infectious Diseases*, 156(1):243–44.
Chowdhury et al., 1991, *Indian Journal of Medical Research*, [A]93:33–36.
Shalinsky et al., 1989, *Prostaglandins*, 37(1):135–48.
Focke et al., 1990, *FEBS Letters*, 261(1):106–08.
Kourounakis et al., 1991, *Research Communications in Chemical Pathology and Pharmacology*, 74(2):249–52.
Liakopoulou–Kyriakides et al., 1985, *Phytochemistry*, 24(3):600–01.
Liakopoulou–Kyriakides, 1985, *Phytochemistry*, 24(7):1593–94.
Nagai, 1973, *Japanese Journal of Infectious Diseases*, 47:321–25.
Bordia, 1978, *Atherosclerosis*, 30:355–60.
Esanu, 1981, *Rev. Roum. Med.–Virol.*, 32(1):57–77.
Tsai et al., 1986, *Chemical Abstracts*, 104(24):No. 61572a.
Bayer et al., 1988, *Planta Medica*, 54(6):560 K1–6.
Block, 1985, *Scientific American*, 252(3):94–99.
Auger et al., 1990, *Chemosphere*, 21(7):837–43.
Jansen et al., 1987, *Planta Medica*, 53(6):559–62.
Yu et al., 1989, *Journal of Food Science*, 54(4):977–81.
Saito et al., 1989, *Journal of the Association of Analytical Chemists*, 72(6):917–20.
Ziegler et al., 1987, *Pharmaceutisch Weekblad Scientific Edition*, 9(4):248 (Abstract).
Mochizuki et al., 1988, *Journal of Chromatography*, 455:271–77.
Lancaster et al., 1989, *Phytochemistry*, 28(2):455–60.
Lancaster et al., 1989, *Phytochemistry*, 28(2):461–64.
Ziegler et al., 1989, *Journal of Liquid Chromatography*, 12(1 & 2):199–200.
Ziegler et al., 1989, *Planta Medica*, 55(4):372–78.
Nock et al., 1986, *Archives of Biochemistry and Biophysics*, 249(1):27–33.
Nock et al., 1987, *Plant Physiology*, 85(4):1079–83.
Knobloch et al., 1987, *Pharmaceutisch Weekblad Scientific Edition*, 9:218.
Knobloch et al., 1988, *Planta Medica*, 54(6):562–62, K1–9.
Jansen et al., 1989, *Planta Medica*, 55:434–49.
Jansen et al., 1989, *Planta Medica*, 55:440–45.
Nock et al., 1989, *Phytochemistry*, 28(3):729–31.
Won et al., 1989, *Physiologia Plantarum*, 77(1):87–92.
Fugita et al., 1990, *Arch. of Biol. & Chem.*, 54(4):1077–79.
Rabinkov et al., 1991, *Mechanisms of Action III*, 5:1149 Abstract No. 4509.
Gmelin et al., 1976, *Phytochemistry*, 15(11):1717–21.
Iberl et al., 1990, *Planta Medica*, 56(2):202–11.
Iberl et al., 1990, *Planta Medica*, 56(3):320–26.
Lawson et al., 1991, *Planta Medica*, 57(3):263–70.
Sendl et al., 1991, *Planta Medica*, 57(4):361–62.
Lawson et al., 1991, *Planta Medica*, 57(4):363–70.
Blania et al., 1991, *Planta Medica*, 57:(4):371–75.
Yu et al., 1989, *Journal of Agric. Food Chem.*, 37(3):725–30.
Yu et al., 1989, *Journal of Agric. Food Chem.*, 37(3):730–34.
Yu et al., 1989, *Journal of Food Science*, 54(3):632–35.
Yu et al., 1989, *Journal of Chromatography*, 462:137–45.
Lawson et al., 1991, *Journal of Natural Products*, 54(2):436–44.
Phillips et al., 1988, *Blood*, 71:831–43.
Barbillari et al., 1993, *Proc. Natl. Acad. Sci. USA*, 90:7941.
Blood et al., 1990, *Biochim. Biophys. Acta*, 1032:89–118.
Cheresh et al., 1987, *J. Biol. Chem.*, 262:17703–17711.
Crowe et al., 1991, *Mechanisms and Specificity of HIV Entry into Host Cells*, 57–70.
Diegel et al., 1993, *AIDS Res. Human Retrovir.*, 9:465.
Fecondo et al., 1993, *AIDS Res. Human Retrovir.*, 9:733.
Fujita et al., 1992, *Jpn. J. Cancer Res.*, 83:1317–26.
Golding et al., 1992, *AIDS Res. Human Retrovir.*, 8:1593.
Gruber et al., 1991, *AIDS Res. Human Retrovir.*, 7:45.
Kreis et al., 1993, *Guidebook to the Extracellular Matrix and Adhesion Proteins*, p. 143.
Guo et al., 1993, *J. Immunol.*, 151:2225.
Hansen et al., 1991, *Scan J. Infect. Dis.*, 23:31–36.
Hart et al., 1991, *Cancer and Metastasis Rev.*, 10:115–128.
Hildreth et al., 1989, *Science*, 244:1075–1078.
Honn et al., 1992, *Exp. Cell Res.*, 201:23–32.
Humphries et al., 1986, *Science*, 233:467–70.
Johnson et al., 1989, *Proc. Natl. Acad. Sci. USA*, 86:641–644.
Kalter et al., 1991, *Immunol. Letters*, 30:219.

Kawaguchi et al., 1992, *Jpn. J. Cancer Res.*, 83:1304–1316.
Knudsen et al., 1988, *J. Cell. Physiol.*, 136:471–78.
Kramer et al., 1989, *Cancer Res.*, 49:393–402.
Kramer et al., 1991, *Cancer and Metastasis Rev.*, 10:49–59.
Meerloo et al., 1993, *J. Gen. Virol.*, 74:129.
Mortarini et al., 1992, *Cancer Res.*, 52:4499–4506.
Murata et al., 1992, *Jpn. J. Cancer Res.*, 83:1327–1333.
Nip et al., 1992, *J. Clin. Invest.*, 90:1406–1413.
Orentas et al., 1993, *AIDS Res. Human Retrovir.*, 9:1157.
Pantaleo et al., 1991, *J. Exp. Med.*, 173:511–514.
Pearce–Pratt et al., 1993, *Biology of Reproduction*, 48:431.
Roossien et al., 1989, *J. Cell Biol.*, 108:1979–83.
Saiki et al., 1990, *Jpn. J. Cancer Res.*, 81:660–67.
Saiki et al., 1990, *Jpn. J. Cancer Res.*, 81:668–75.
Saiki et al., 1990, *Jpn. J. Cancer Res.*, 81:1003–1011.
Smole et al., 1992, *FASEB J.*, 6:A1714.
Soszka et al., 1991, *Exp. Cell Res.*, 196:6–12.
Springer, 1990, *Nature*, 346:425.
Thieblemont et al., 1993, *Clin. Exp. Immunol.*, 92:106.
Ugen, 1988, *J. Natl. Cancer Inst.*, 80:1461.
Valentin et al., 1990, *J. Immunol.*, 144:934–937.
Van Muijen et al., 1991, *Int. J. Cancer*, 48:85–91.
Vermot–Desroches et al., 1991, *Molec. Immunol.*, 28:1095.
Vink et al., 1993, *Lab Invest.*, 68:192–203.
Vogel et al., 1993, *J. Cell Biol.*, 121:461.
Golding et al., 1992, *AIDS Res. Human Retrovir.*, 8:918.
Hermanowski–Vosatka et al., 1992, *Cell*, 68:341–52.
Pantaleo et al., 1991, *Eur. J. Immunol.*, 21:1771–74.
Patarroyo et al., 1990, *Immunol. Rev.*, pp. 67–108.
Bachelot et al., 1992, *Biochem J.*, 284:923–28.
Lawson et al., 1992, *Thrombosis Research*, 65:141–56.
Oelkers et al., 1992, *Arzneim.–Forsch/Drug Res.*, 42:136–39.
Sendl et al., 1992, *Ahterosclerosis*, 94:79–95.
Sendl et al., 1992, *Planta Med.*, 58:1–7.
Siegel et al., 1991, *Z. Kardiologie 80 Supp.* 7, pp. 9–24.
Singh et al., 1992, *Mycologia*, 84:105–108.
Tadi et al., 1991, *Anticancer Research*, 11:2037–2042.
Acosta et al., 1994, *Am. J. Hosp. Pharm.*, 51:2251–2267.
Allen et al., 1995, *Medical Hypotheses*, 45:164–168.
Altieri et al., 1988, *Leukocyte Fibrinogen Receptor*, pp. 1893–1900.
Arthur et al., 1992, *Science*, 258:1935–1938.
Asselot–Chapel et al., 1993, HIV1 Infection of Macrophages Results in Modulation of Fibronectin and α5β1 Integrin Biosynthesis, IX International Conference on AIDS, PO–A12, p. 169.
Birdsall et al., 1994, *Journal of Leukocyte Biology*, 56:310–317.
Blobel et al., 1992, *Nature*, 356:248–252.
Bourinbaiar et al., 1993, *Acta. Virol.*, 37:21–28.
Bourinbaiar et al., 1994, *Cellular Immunology*, 155:230–236.
Bridges et al., 1994, *Antiviral Research*, 25:169–175.
Butera et al., 1992, *AIDS Res. and Human Retrovir.*, 8(6):991–995.
Butini et al., 1993, ICAM–1/2/3 Molecules Function as Counter–Receptors for LFA–1 in HIV–Mediated Syncytia Formation, IX International Conference on AIDS, PO–A14, p. 182.
Butini et al., 1994, *Eur. J. Immunol.*, 24:2191–2195.
Carlos et al., 1990, *Immunological Reviews*, 114:5–28.
Chehimi et al., 1993, *Journal of General Virology*, 74:1277–1285.
Clapham et al., 1993, *Phil. Trans. R. Soc. Lond. B*, 342:67–73.
Coller et al., 1989, *Circulation*, 80(6):1766–1774.
Collman et al., 1992, *Seminars in Virology*, 3:185–202.
Connor et al., 1994, *The New England J. of Medicine*, 331(18):1173–1180.
Cook et al., 1993, *Thrombosis and Haemostasis*, 70(5):838–847.
Denis, 1994, *The Journal of Immunology*, 153:2072—2081.
Douglas et al., 1994, *Journal of Reproductive Immunology*, 24:49–62.
Dullege et al., 1992, VIII International Conference on AIDS, PoB 3028.
Falanga et al., 1991, *Eur. J. Immunol.*, 21:2259–2263.
Faurc et al., 1994, *Virus Research*, 34:1–13.
Ferguson et al., 1991, *Proc. Natl. Acad. Sci. USA*, 88:8072–8076.
Fletcher et al., 1993, *Journal of Clinical Pharmacy and Therapeutics*, 18:375–388.
Gehlsen et al., 1992, *Clin. Exp. Metastasis*, 10:111–120.
Glander et al., 1993, *International Journal of Andrology*, 16:105–111.
Gonzalez–Scarano et al., 1992, *Seminars in Virology*, 3:225–234.
Gougeon et al., 1993, *Science*, 260:1269–1270.
Grau et al., 1991, *Eur. J. Immunol.*, 21:2265–2267.
Guo et al., 1995, *AIDS Res. and Human Retrovir.*, 11:1007–1013.
Hamilton et al., 1992, *The New England Journal of Medicine*, 326:437–443.
Hardan et al., 1993, *Int. J. Cancer*, 55, 1023–1028.
Harning et al., 1993, *Clin. Exp. Metastasis*, 11:337–342.
Haynes, 1993, *Science*, 260:1279–1286.
Huitinga et al., 1993, *Eur. J. Immunol.*, 23:709–715.
Isberg et al., 1994, *Trends in Microbiology*, 2(1):10–14.
Ishizuka et al., 1993, *Int. J. Immunopharmacol.*, 17(2):133–139.
Ito et al., 1992, *Journal of Virology*, 66(17):5999–6007.
Johnson, 1992, *AIDS Clinnical Review*, pp. 70–104.
Johnston, 1993, *Science*, 260:1286–1293.
Kavanaugh et al., 1994, *Arthritis & Rheumatism*, 37:992–999.
Kazazi et al., 1994, *Journal of General Virology*, 75:2795–2802.
Kolson et al., 1993, *AIDS Res. and Human Retrovir.*, 9(7):677–685.
Larson et al., 1990, *Immunological Reviews*, 114:181–216.
Levy, 1991, *Adv. Exp. Med. Biol.*, 300:1–15.
Li et al., 1995, *Science*, 268:429–431.
Locher et al., 1994, *Clin. Exp. Immunol.*, 98:115–122.
Mitsuya et al., 1991, *The FASEB Journal*, 5:2369–2381.
*MMWR (Morbidity and Mortality Weekly Report*, 43(16):285–287, 1994.
Mohan, 1993, *Drug Development Research*, 29:1–17.
Mould et al., 1991, *The Journal of Biological Chemistry*, 266(6):3579–3585.
Mousa et al., 1994, *Circulation*, 89(1):3–12.
Nemerow et al., 1994, *Trends in Cell Biology*, 4:53–55.
Ohta et al., 1994, *The EMBO Journal*, 13(9):2044–2055.
Palmer et al., 1993, *Clin, Exp. Immunol.*, 93:344–349.
Pantaleo et al., 1994, *Current Opinion in Immunology*, 6:600–604.
Paul, 1995, *Science*, 267:633–636.

Perez, 1994, *Antimicrobial Agents and Chemotherapy*, 38(2):337–339.
Phillips, 1994, *AIDS*, 8:719–731.
Reinhardt et al., 1993, IX International Conference on AIDS, PO–A14–0285, p. 182.
Reynolds–Kohler et al, 1991, *Mechanisms and Specificity of HIV Entry Into host Cells*, pp. 27–44.
Rossen et al., 1989, *Trans. Ass. Am. Physicians*, 102:117–130.
Sato et al., 1992, *Virology*, 186:712–724.
Scarborough et al., 1993, *The Journal of Biological Chemistry*, 268(2):1058–1065.
Schuitemaker et al., 1992, *Journal of Virology*, 66(3):1354–1360.
J.C., 1993, *Science*, 260:1256.
Shebuski et al., 1990, *Thrombosis and Haemostasis*, 64(4):576–581.
Sheu et al., 1994, *J. Lab. Clin. Med.*, 123(2):256–263.
Stent et al., 1994, *Journal of Leukocyte Biology*, 56:304–309.
Stevenson et al., 1992, *AIDS Res. and Human Retrovir.*, 8(2):107–117.
Tabata et al., 1994, *J. Immunol.*, 153:3256–3266.
Taichman et al., 1991, *Cell Regulation*, 2:347–355.
Tang et al., 1993, *Int. J. Cancer*, 54:338–347.
Tcheng et al., 1994, *Circulation*, 90(4):1757–1764.
Trikha et al., 1994, *Cancer Research*, 54:4993–4998.
Weeks et al., 1991, *J. Cell Biol.*, 114:847–853.
Aboulker et al., 1993, *The Lancet*, 341:889–890.
Yarchoan et al., 1992, *J. Enzyme Inhibition*, 6:99–111.
Yarchoan et al., 1991, *Blood*, 78(4):859–884.
Zahalka et al., 1993, *J. Immunol.*, 150:4446–4477.
Adler et al., 1992, *Biochemistry*, 31:1031–1039.
Adler et al., 1991, *Science*, 253:445–448.
Adler et al., 1993, *Biochemistry*, 32:282–289.
Au, et al., 1991, *Biochemical and Biophysical Research Communications*, 181(2):585–593.
Calvete et al., 1991, *Biochemistry*, 30:5225–5229.
Calvete, et al., 1992, *FEBS Letters*, 309(3):316–320.
Chang, et al., 1993, *Biochemical and Biophysical Research Communications*, 190(1):242–249.
Chao, et al., 1989, *Proc. Nat'l Acad. Sci. USA*, 86:8050–8054.
Chen, et al., 1991, *Biochemistry*, 30:11625–11636.
Cooke et al., 1991, *Eur. J. Biochem*, 202:323–328.
Dalvit et al., 1991, *Eur. J. Biochem*, 202:315–321.
Dennis et al., 1990, *Proc. Nat'l Acad. Sci. USA*, 87:2471–2475.
Dennis et al., 1993, *Proteins: Structure, Function and Genetics*, 15:312–321.
Fecondo, et al., 1993, *Aids Research and Human Retroviruses*, 9(8):733–740.
Gan, et al., 1988, *The Journal of Biological Chemistry*, 263(36):19827–19832.
Garsky et al., 1989, *Proc. Nat'l Acad. Sci. USA*, 86:4022–4026.
Glaser, 1995, *Genetic Engineering News*, 15(20):6–7.
Gould et al., 1990, *P.S.E.B.M.*, 195:168–171.
Hardan, I., et al., 1993, *Int. J. Cancer*, 55:1023.
Hite, et al., 1992, *Biochemistry*, 31:6203–6211.
Hite, et al., 1994, *Archives of Biochemistry and Biophysics*, 308(1):182–191.
Huang et al., 1991, *Biochimica et Biophysica Acta*, 1074:144–150.
Huang et al., 1991, *Biochimica et Biophysica Acta*, 1074:136–143.
Huang et al., 1991, *J. Biochem.*, 109:328–334.
Huang et al., 1991, *Biochemical Pharmacology*, 42(6):1209–1219.
Huang et al., 1991, *Biochem J.*, 277:351–357.
Huang, et al., 1997, *The Journal of Biological Chemistry*, 262(33):16157–16163.
Huang, et al., 1989, *Biochemistry*, 28:661–666.
Humphries, M.J., et al., 1988, *J. Clin. Invest.*, p. 782.
Kini et al, 1990, *Toxicon*, 28(12):1387–1422.
Kini et al., 1992, *Toxicon*, 30(3):265–293.
Knudsen, et al., 1988, *Experimental Cell Research*, 179:42–49.
Mazur et al., 1991, *Eur. J. Biochem.*, 202:1073–1082.
Musial, et al., 1990, *Circulation*, 82:261–273.
Neeper et al., 1990, *Nucleic Acids Research*, 18(14):4255.
Omori–Satoh, et al., 1986, *Toxicon*, 24(11–12):1045–1053.
Paine et al., 1992, *The Journal of Biological Chemistry*, 267(32):22869–22876.
Perez, et al., 1994, *Antimicrobial Agents and Chemotherapy*, 38:337–339.
Rucinski et al., 1990, *Biochimica et Biophysica Acta*, 1054:257–262.
Sato, et al., 1990, *Journal of Cell Biology*, 111:1713–1723.
Saudek et al., 1991, *Biochemistry*, 30:7369–7372.
Saudek et al., 1991, *Eur. J. Biochem*, 202:329–338.
Savage et al., 1990, *The Journal of Biological Chemistry*, 265(20):11766–11772.
Scarborough et al., 1993, *The Journal of Biological Chemistry*, 268(2):1066–1073.
Scarborough et al., 1991, *The Journal of Biological Chemistry*, 266(15):9359–9362.
Scarborough et al., 1993, *The Journal of Biological Chemistry*, 268(2):1058–1065.
Seymour et al., 1990, *The Journal of Biological Chemistry*, 265(17):10143–10147.
Shebuski et al., 1989, *The Journal of Biological Chemistry*, 264(36):21550–21556.
Shebuski et al., 1990, *Circulation*, 82:169–177.
Sheu et al., 1992, *Jpn. J. Cancer Res.*, 83:885–893.
Soszka et al., 1991, *Experimental Cell Research*, 196:6–12.
Takeya, et al., 1990, *The Journal of Biological Chemistry*, 265(27):16068–16073.
Takeya et al., 1992, *The Journal of Biological Chemistry*, 267(20):14109–14117.
Takeya et al., 1993, *J. Biochem*, 113:473–483.
Weber, et al., 1992, *Planta Med.*, 58:417–423.
Williams, et al., 1990, *Biochimica et Biophysica Acta*, 1039:81–89.
Yamakawa et al., 1991, *J. Biochem.*, 109:667–669.
Bone, 1991, *Annals of Internal Medicine*, 115:457–469.
Broaddus et al., 1994, *Journal of Immunology*, 152:2960–2967.
Feuerstein et al., 1987, *Am. Rev. Pharmacol. Toxicol.*, 27:301–313.
Fleckenstein et al., 1991, *Circulatory Shock*, 35:223–230.
Hub et al., 1996, *Chemoattractant Ligands And Their Receptors*, Chpt. 13, pp. 301–325.
Harlan et al., 1992, *Adhesion*, Chpt. 6, pp. 117–150.
Henderson, 1994, *Ann. Intern. Med.*, 121:684–697.
Hirvonen et al., 1989, *Z. Rechtsmed.*, 102:297–304.
Hsueh et al., 1986, *AJP*, 122(2):231–239.
Kellermann et al., 1989, *Klin Wochenschr*, 67:190–195.

Kishimoto et al., 1992, *Inflammation: Basic Principles And Clinical Correlates*, 2nd Ed., Chapter 20, pp. 353–406.
Lewis et la., 1990, *Mechanisms Of Disease*, 323(10):645–655.
Liu et al., 1992, *Adhesion*, Appendix, pp. 189–193.
Liu et al., 1992, *Adhesion*, Chapter 8, pp. 183–187.
Mosby, 1990, *Multiple Organ Failure: Patient Care and Prevention*, Chapter 10, pp. 235–263.
Mosby, 1990, *Multiple Organ Failure: Patient Care and Prevention*, Chapter 26, pp. 473–486.
Mukaida et al., 1996, *Journal Of Leukocyte Biology*, 59:145–151.
Ogata et al., 1992, *Infection And Immunity*, 60(6):2432–2437.
Perbeck et al, 1980, *Acta Chir Scand*, 500(supp):91–94.
Shenep et al., 1984, *The Journal Of Infectious Diseases*, 150(3):380–388.
Simon et al., 1992, *Inflammation: Basic Principles and Clinical Correlates*, 2nd Ed., Chapt. 51, pp. 999–1016.
Spannagl et al., 1991, *Thrombosis Research*, 61:1–10.
Stevens et al., 1986, *J. Clin Invest.*, 77:1812–1816.
Svartholm et al., 1987, *Circulatory Shock*, 22:291–301.
Svartholm et al., 1987, *Circulatory Shock*, 22:173–183.
Terashita et al., 1987, *The Journal Of Pharmacology And Experimental Therapeutics*, 243(1):378–383.
Thörne et al., 1986, *Circulatory Shock*, 20:61–69.
Tracey, 1991, *Circulatory Shock*, 35:123–128.
VanOtteren et al., 1995, *The Journal Of Immunology*, 154:1900–1908.
Watanabe et al., 1995, *International Immunology*, 7(7):1037–1046.
Bianchi et al., 1991, *Haematologica*, 76:383–388.
Bishop, 1991, *Cell*, 64:235–248.
Brodt et al., 1990, *Breast Cancer Research and Treatment*, 17:109–120.
Brodt, 1991, *Cancer and Metastasis Reviews*, 10:23–32.
Bukowski et al., 1991, *Journal of Immunotherapy*, 10:432–439.
Chambers et al., 1992, *Anticancer Research*, 12:43–48.
Chammas et al., 1991, *Tumor Biol.*, 12:309–320.
Dedhar, 1990, *BioEssays*, 12(12):583–590.
Felding–Habermann et al., 1992, *J. Clin. Invest.*, 89:2018–2022.
Giancotti et al., 1994, *Biochimica et Biophysica Acta*, 1198:47–64.
Heicappell et al., 1991, *World Journal of Urology*, 9:204–209.
Horst et al., 1991, *Leukemia*, 5(10):848–853.
Hermann et al., 1991, *Cancer Immunology Immunotherapy*, 34:111–114.
Hsiao et al., 1991, *J. Clin Invest.*, 87:811–820.
Ingber, 1992, *Seminars In Cancer Biology*, 3:57–63.
Inghirami et al., 1990, *Science*, 250:682–686.
Juliano et al., 1993, *Current Opinion In Cell Biology*, 5:812–818.
Kortlepel et al., 1991, *Leukemia*, 7(8):1174–1179.
Kramer et al., 1991, *Cell Regulation*, 2:805–817.
Krief et al., 1989, *Int. J. Cancer*, 43:658–664.
Mortarini et al., 1992, *Cancer Research*, 52:4499–4506.
Mueller et al., 1991, *Antibody, Immunoconjugates, and Radiopharmaceuticals*, 4(2):99–106.
Olive et al., 1991, *Journal Of Immunotherapy*, 10:412–417.
Pignatelli et al., 1991, *Journal Of Pathology*, 165:25–32.
Plantefaber et al., 1989, *Cell*, 56:281–290.
Postigo et al., 1991, *J. Exp. Med.*, 174:1313–1322.
Ramachandrula et al., 1992, *Journal of Cell Science*, 101:859–871.
Ramos et al., 1991, *Invasion Metastasis*, 11:125–138.
Schreiner et al., 1991, *Cancer Research*, 51:1738–1740.
Van Waes et al., 1992, *Molecular Biology And Genetics*, 25(5):1117–1139.
Wake et al., 1995, *Blood*, 86(6):2257–2267.
Witjies et al., 1995, *Carcinogenesis*, 16(11):2825–2832.
Zutter et al., 1990, *American Journal Of Pathology*, 137(4):863–870.
Belman et al., *Chem. Abstracts*, 112:91227 (1990).
Belman et al., *J. Biochem. Toxicol.*, 4:151–160 (1989).
Lichtenstein et al., *Chem. Abstracts*, 104, 45756h, (1986).
Saeed et al., *Chem. Abstracts*, 107:400435 (1987).
Saeed et al., *J. Pharm.*, 6:77–82 (1985).
Wagner et al., *Chem. Abstracts*, 107:489878 (1987).
Wagner et al., *Planta Med.*, 53:305–306 (1987).
Wakunaga Seiyaku KK, Derwent WIPDS, Abstract Corresponding to JP 62 129224 (1987).
Hemler, in Guidebook to the Extracellular Matrix, pp. 143–145 (Kreis and Vale eds. 1993).
Buchanan et al., *J. Thorc. Cardiovasc. Surg*, 111:941–7 (1996).
Hynes, *Cell*, 69:11–25 (1992).
Ikeda et al., *Infection and Immunity*, 63(12):4812–4817 (1995).
Issekutz et al., *J. Exp. Med.*, 181:1197–1203 (1995).
Issekutz et al., *J. Exp. Med.*, 183:2175–2184 (1996).
Mazzone et al., *Haematologica*, 80:161–175 (1995).
Talbott et al., *New Horizons*, 2(4):545–554 (1994).
Vedder et al., *Surgery*, 106:509–16 (1989).
Vedder et al., *J. Clin. Invest.*, 81:939–944 (1988).
Ledezma et al, Derwent Drug File Abstracts, abstract No. 97–04360, 1996.*
Perez et al, Chemical Abstracts, vol. 120, abstract No. 182454, 1994.*

* cited by examiner

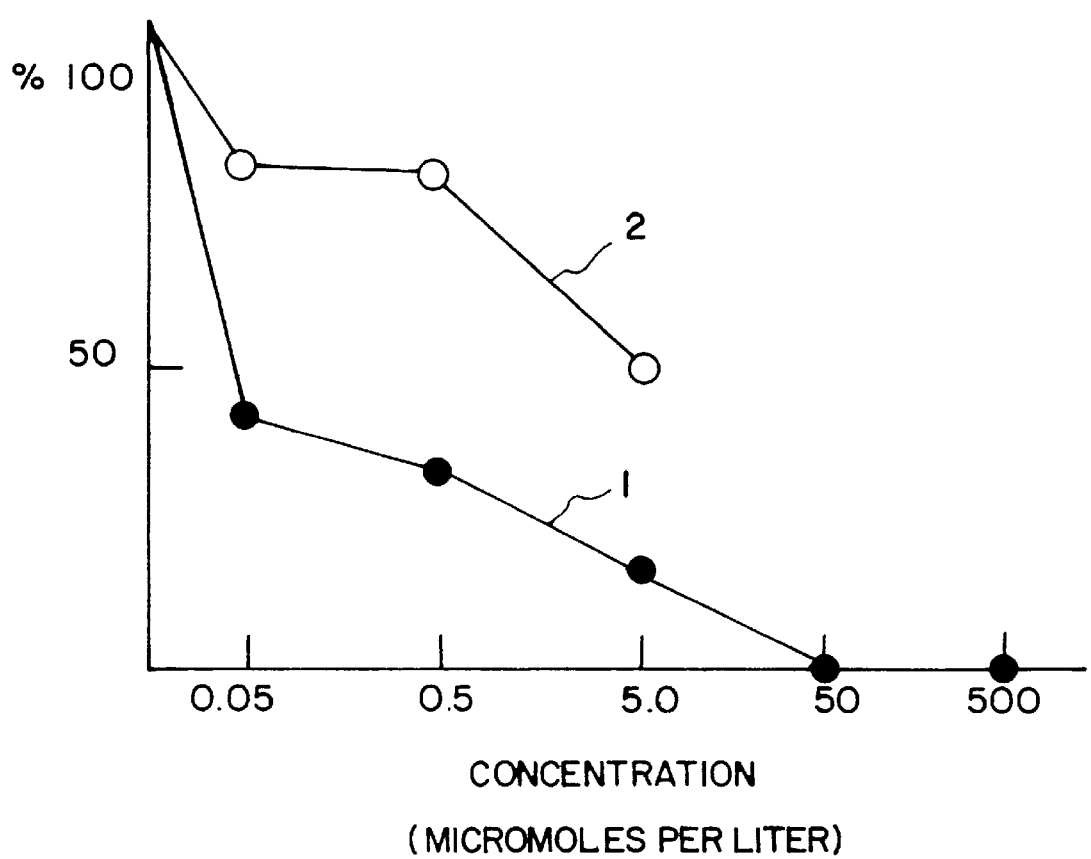

METHODS OF USING INTEGRIN MODULATORS FOR TREATMENT OF INFLAMMATION

This application is a continuation-in-part of PCT application PCT/US97/00583, filed Jan. 13, 1997, which was a continuation-in-part of application Ser. No. 08/698,893, filed Aug. 16, 1996, now abandoned, which was a continuation-in-part of application Ser. No. 08/585,190 filed Jan. 11, 1996, now U.S. Pat. No. 5,948,821 which was a continuation-in-part of application Ser. No. 08/445,146, filed May 19, 1995, now abaondoned which was a continuation-in-part of application Ser. No. 07/906,850, filed Jun. 30, 1992, now abandoned.

BACKGROUND OF THE INVENTION

Integrins are heterodimeric transmembrane glycoproteins which act, inter alia, as cell receptors for surface molecules of other cells and for extracellular matrix (ECM) proteins, herein termed collectively "integrin ligands." Both soluble and immobilized integrin ligands are known to be ordinarily bound by integrins. Integrins are found on most types of cells. Ligand binding by integrins may result in a series of additional cellular events. When these additional events occur, they involve one or more cellular functions. These cellular events and functions, some of which are discussed below for illustrative purposes, are integrin-mediated. For a general review of integrins, see, *Guidebook to the Extracellular Matrix and Adhesion Proteins* (Kreis, et al., Eds.), 1993, and Pigot, et al., *The Adhesion Molecule Facts Book*, Academic Press, 1993.

One such integrin-mediated cellular function is signaling. For instance, certain integrins are known to transfer information from the inside to the outside of the cell (inside-out signaling), and/or from the outside to the inside of the cell (outside-in signaling), although other types of signaling may also occur. An example of inside-out signaling is the process whereby an integrin acquires affinity for ligands in response to cell activation-associated intracellular events (integrin upregulation). Binding of integrin ligands to certain integrins (e.g., in the case of integrin-mediated cell adhesion) may initiate signal transduction events, in a manner similar to that described for other cell surface receptors. The signals thus elicited are termed outside-in signals and regulate various cell responses, such as gene expression, cell differentiation, and cell proliferation.

Signaling may result in integrin clustering, i.e., the association of integrins with each other (and other molecules) by lateral interactions. The formation of such clusters may influence various integrin functions in multiple ways, including, for example, by secondary signaling.

The integrin-mediated function of adhesion is important for a variety of physiological and pathological responses. The extent of adhesion is controlled by integrin signaling. For example, as a result of initial integrin-dependent adhesion to a substratum, certain cells change their shape and start spreading on its surface, using integrins for establishing new contacts with the underlying proteins (e.g., ECN components). In motile cells, the whole array of integrin-mediated events involving adhesion—initial contact, cell shape change, cell spreading, and cell locomotion—is sometimes termed "the adhesion cascade" (Sharar, S.R., et al., The Adhesion Cascade and Anti-Adhesion Therapy: An Overview, 16 *Springer Semin. Immunopathol.* 359, 1995). Examples of adhesion cascades include tumor cell metastasis, cell migration processes associated with wound healing, and lymphocyte homing, although similar cascade mechanisms are operative in the absence of locomotion (e.g., platelet adhesion and aggregation). Extravasation of neutrophils is described below in greater detail, as a paradigmatic integrin-driven adhesion cascade (Hub, E., et al., Mechanism of Chemokine-Induced Leukocyte Adhesion and Emigration, *Chemoattractant Ligands and Their Receptors* (Horuk, R., Ed.), Boca Raton, CRC Press, 1996, 301).

The onset of extravasation is signaled by the appearance in the circulation of chemotactic factors, or chemoattractants (i.e., specific substances that initiate cell migration along their concentration gradients). Chemoattractants (e.g., chemokines, bacterial peptides, and products of complement activation) activate neutrophils and upregulate their integrin receptors (neutrophil integrins include, e.g., LFA-1 [CD11a/CD18], CR3 [also known as Mac-1, CD11b/CD18], and gp150,95 [CD11c/CD18].) As a result, the activated neutrophils adhere to endotheliocytes, change shape, and spread on the endothelial surface. Thereafter, the motile apparatus of the neutrophils is stimulated by the chemoattractants, and they start migrating, first across the endothelial layer and further, through the perivascular ECK, towards the source of the chemotactic stimulus, e.g., pathogenic bacteria invading a certain bodily tissue. During the whole process, from the initial firm contact with the endothelium to the cessation of locomotion at the destination site, various integrins serve to attach the neutrophil to the substrata it encounters, enabling its recruitment to the locus of infection.

Another integrin-mediated function is cell-to-cell fusion. Under physiological conditions, fusion is a developmentally regulated stage in the differentiation of certain multinucleate cells (e.g., osteoclasts, myocytes, and syncytiotrophoblasts) and a prerequisite to fertilization (in the case of sperm-egg fusion). Fusion is effected by specialized cellular systems involving integrins (see, e.g., refs. cited in Huovila, A.-P.J., et al., ADAMs and Cell Fusion, 8 *Current Olin. Cell. Biol.* 692, 1996 and Ohgimoto, S., et al., Molecular Characterization of Fusion Regulatory Protein-1 [FRP-1] that Induces Multinucleate Giant Cell Formation of Monocytes and HIV gp160-Mediated Cell Fusion: FRP-1 and 4F2/CD98 Are Identical Molecules, 155 *J. Immunol.* 3585, 1995).

The ability to undergo recirculation from intracellular compartments to the cell surface and vice versa is a common property of divers cellular receptors, including integrins (see, e.g., Handagama, P., et al., Kistrin, an Integrin Antagonist, Blocks Endocytosis of Fibrinogen into Guinea-Pig Megakaryocyte and Platelet α-Granules, 91 *J. Clin. Invest.* 193, 1993). This capability of integrins serves to mediate other cellular functions by transporting into the cell extracellular material (e.g., soluble proteins, particulate matter, and other cells). Integrin-mediated internalization is used by certain microorganisms to invade their targets. For example, CR3 mediates entry of iC3b-opsonized HIV-1 and HIV-2 into CD4-negative lymphocytic and monocytic cells (Boyer, V., et al., Complement Mediates Human Immunodeficiency Virus Type 1 Infection of a Human T cell Line in a CD4- and Antibody-Independent Fashion, 173 *J. Exp. Med.* 1151, 1991).

The above-delineated functions of integrins are illustrative only, as other characterizations of integrin functions can also be made. Moreover, the integrin-mediated functions as delineated herein are overlapping and interrelated. In the case of neutrophil extravasation, for example, the initial chemotactic signal activating the cells results in integrin upregulation (inside out signalina) and adhesion to the endothelial surface. This adhesion event, in turn, elicits an outside-in signal, enabling the neutrophil to change its shape, which is a prerequisite to spreading and migration. Likewise, when the neutrophil that has arrived to the source of chemoattractants adheres to the bacteria, an outside-in signal transduced via the involved integrins initiates their internalization, together with the attached bacteria (phagocytosis).

Furthermore, regarding outside-in integrin signaling, certain cellular processes are coregulated by several distinct signaling systems acting in a concert. In the case of neutrophils extravasating to the tissues to phagocytose bacteria, the cells receive signals via distinct integrins (first from those that attach it to the substratum and subsequently from those recognizing the bacteria) and the receptors of the chemoattractant (along the concentration gradient of which the movement occurs). This interplay of signals regulates the antibacterial machinery of the neutrophils in such a way that only upon contact with the bacteria, which is established via a particular type of integrin, are the constituents of the intracellular granules released and reactive oxygen species formed. As a result, the formation and release of microbicidal substances take place preferentially at sites of contact with bacteria, enabling their effective killing and preventing the destruction of host tissue (Wright, S. D., Receptors for Complement and the Biology of Phagocytosis [Chapter 25], *Inflammation: Basic Principles and Clinical Correlates* [Gallin, J. I., et al., Eds.], 2nd Ed., New York, Raven Press, 477, 1992).

The present invention involves the regulation of a broad range of cellular activities by modulating certain integrin functions. One prototype integrin modulator of the present invention is Ajoene. Ajoene is 4,5,9-trithiadodeca-1,6,11-triene-9-oxide, having a structural formula as follows:

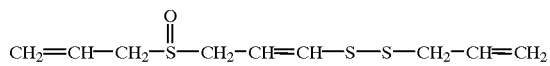

Ajoene, and a precursor thereof, can be isolated from extracts of garlic (*Allium sativum*). As the garlic is crushed, alliin in the garlic comes into contact with allinase in the cell wall to form allicin. Then, in the presence of a polar molecule, such as a lower alcohol or even water, allicin forms Ajoene.

Ajoene has been previously shown to inhibit platelet aggregation by inactivating allosterically the platelet integrin, GP IIb/IIIa (Apitz-Castro, R., et al., 141 *Biophys. Res. Commun.* 145, 1986). This inhibition of integrins by Ajoene is reversible.

SUMMARY OF THE INVENTION

The invention provides methods of treating a variety of diseases and conditions by administering an effective amount of an integrin modulating agent, as further defined and specified herein, to an animal suffering from one of the diseases or conditions. In particular, the invention provides: (1) a method of treating inflammation; (2) methods of treating and preventing viral infections; (3) a method of treating shock; (4) a method of treating arthritis; (5) a method of contraception; (6) a method of suppressing immune responses; (7) a method of treating an autoimmune disease; (8) a method of inhibiting undesirable integrin-mediated cell-cell fusion; (9) a method of inhibiting the formation of lesions; (10) a method of treating psoriasis; (11) a method of treating atherosclerosis; (12) a method of treating diseases or conditions involving a plurality of integrin-dependent etiopathogenetic mechanisms; and (13) a method of inhibiting the transfer of genetic material.

In addition, the invention provides a method of treating a tissue by contacting the tissue with an integrin modulating agent. Such treatment improves the condition of the tissue for subsequent use, as compared to tissue which is not treated with an integrin modulating agent. In particular, tissue which is to be transplanted into a recipient may be treated with an integrin modulating agent, and the chances of the tissue being successfully transplanted will be increased.

The preferred integrin modulating agents are ajoene and disintegrins, variants and analogs of disintegrins.

BRIEF DESCRIPTION OF THE DRAWING

FIG. 1 is a graph of HIV-induced syncytium formation (curve 1) or HIV replication (curve 2) as a percentage of untreated control versus concentration of ajoene (micromoles per liter).

For curve 1, the effect of Ajoene on the fusion of cultured, intact H9 cells with HIV infected $H9_{RF}$ cells is disclosed. For this curve, the vertical graph axis pertains to the maximum amount of syncytia formed in the absence of Ajoene (100 percent), while the points on line 1 represent percentages of such an amount of syncytia formed in the presence of varying concentrations of Ajoene (micromoles per liter). The $IC_{50}$ of syncytium formation was found at a concentration of 0.045 micromole of Ajoene per liter. Essentially no syncytia were found at a concentration of 50 micromoles of Ajoene per liter.

Referring to curve 2, the antiviral activity of Ajoene is shown, as assessed by the inhibition of $HIV-1_{Lav-BRU1}$ replication in cultured CEM13 cells. Here, the vertical axis represents the percentage of HIV antigens detected by solid phase immunoassay in the absence of Ajoene. The $IC_{50}$ was achieved under these conditions at about a 5 micromolar concentration of Ajoene.

DETAILED DESCRIPTION OF THE PRESENTLY PREFERRED EMBODIMENTS

By this invention, safe and effective doses of Ajoene may inhibit the progression of an HIV infection in a patient. Specifically, stereoisomer mixtures of Ajoene may be used, although pure (E) and (Z) stereoisomer forms may also be used.

One of the characteristics of an HIV infection so inhibited is the formation of HIV-induced syncytia, in which HIV target cells such as lymphocytes and monocytes fuse together to form giant, multinucleate cells in HIV-infected patients. This inhibiting effect would require a sufficient dose to provide a concentration of Ajoene of at least 50 nanomoles of Ajoene per liter of blood plasma in the patient, and, if a single dose is used, preferably at least 5 micromoles of Ajoene per liter of a patient's blood plasma, although lesser quantities may also suffice. Transfer of genetic material between cells will, thereby, also be inhibited by Ajoene.

Additionally, it appears that Ajoene inhibits the entry of the infective HIV material into its target cells, including CD4-negative cells, both virus-to-cell and cell-to-cell, and the production of HIV and other viruses by the infected cells. For these purposes, Ajoene is preferably administered in a sufficient dose to provide a concentration approaching or exceeding 5 micromoles of patient's blood plasma, although lesser concentrations may also be effective. In the particular case of CD4-negative cells, Ajoene is preferably administered in sufficient dose to provide a concentration approaching or exceeding 200 micromoles of patient's blood plasma, although lesser concentrations may be effective.

In addition to infections caused by HIV and other viruses of the Retroviridae family, Ajoene can be used to treat infections caused by Herpesviridae (e.g., herpes simplex, varicella zoster, Epstein-Barr virus, and cytomegaly virus), Hepadnaviridae (e.g., hepatitis B), Picornaviridae (e.g., hepatitis A virus and poliomyelitis virus), Orthomyxoviridae (e.g., influenza virus), Poxviridae (e.g., variola virus and vaccinia virus), Flaviviridae (e.g., yellow fever virus and hepatitis C virus), Rubiviridae (e.g., rubella virus), Paramyxoviridae (e.g., measles, parainfluenza, mumps and canine distemper viruses), Rhabdoviridae (e.g., rabies virus), Papovaviridae (e.g., papillomavirus), and Adenoviridae.

Ajoene also serves as an agent that inhibits the adhesion and aggregation of blood cells, such as platelets and neutrophils. Ajoene, therefore, exhibits benefit as an agent for the treatment of pathologies derived from adhesion and aggregation of these and other cells, including various types of inflammation.

Inflammation, a pathological process inherent in a variety of distinct diseases and illnesses, is defensive in nature, but potentially dangerous if uncontrolled. When viewed at the "whole body" level, an inflammation is most frequently characterized by several localized manifestations (indices), including hemodynamic disorders (e.g., hyperemia and edema), pain, temperature increment, and functional lesion. These inflammatory phenomena are underlain by changes at the cellular and molecular levels. At the cellular level, inflammation is characterized by leukocyte extravasation (a process involving adhesion of leukocytes to the endothelium of the vessel wall and migration into tissue where they may phagocytose bacteria, viruses, and cell debris) and platelet aggregation (a mechanism whereby the spread of the infection is prevented). At the molecular level, inflammation is characterized by activation of at least three plasma defense systems (complement, kinin, and coagulation/fibrinolysis cascades) and by synthesis of cytokines and eicosanoids. When inflammation becomes generalized, as in the case of shock, various indices of inflammation occur systemically throughout the entire organism.

In cases of shock, platelets and leukocytes (principally neutrophils) aggregate in the blood vessels, leading to the development of a clinical condition known as multiple organ failure. The primary organ affected in shock patients is commonly the lung. Lung failure, or adult respiratory distress syndrome (ARDS), a destructive inflammation resulting from adhesion, aggregation, and degranulation of activated neutrophils in the pulmonary microvasculature, may be the main cause of death in patients suffering shock. Ajoene may thus counteract at least part of the effects of shock, whether arising, for example, from sepsis, anaphylaxis, or from blood loss. The inhibiting effect of Ajoene in this use would typically be the result of a dose to provide a concentration of Ajoene approaching or exceeding 5 micromoles per liter of the patient's blood plasma, and, in the case of a single dose, preferably approaching or exceeding 100 micromoles per liter of the patient's blood plasma, although lesser concentrations may be effective.

Ajoene can also be administered in effective dosages to suppress many other acute inflammatory processes, such as those associated with peritonitis, meningitis, and ischemia-reperfusion. Ischemia-reperfusion injury occurs in heart, brain, kidney, liver, lung, or intestinal tract when blood supply to these organs is abruptly stopped (ischemia) and then resumed (reperfusion) after a short period.

With the onset of ischemia and the decrease in the perfusion pressure, neutrophils (because they are larger and less deformable than erythrocytes) are retained in the capillaries. As the ischemia progresses, cytokines (and other chemoattractants) that are released into the capillary lumina increase the adhesiveness of the retained neutrophils to the endothelium and to each other. Aggregates of neutrophils thus formed obstruct postcapillary venules ("no-reflow," or "no-washout") and attenuate the restoration of the blood flow in the affected region, precluding its reoxygenation and extending the area of ischemia. Activated neutrophils trapped in the capillaries release hydrolytic enzymes and reactive oxygen species (i.e., the armamentarium ordinarily used to defend the host against microorganisms), producing a destructive inflammation.

Restoration of the blood flow, however, further augments the severity of the inflammation thus developed. Neutrophils arriving to the previously ischemic region are activated (by chemoattractants and/or products released by the trapped neutrophils) and recruited into the tissue, where the defensive machinery of the cells is once again used against the host (secondary injury). Notably, ischemia-reperfusion produces a more extensive injury than ischemia per se, which accounts for the tissue damage observed in various diseases and states, such as myocardial infarction, intestinal necrosis, and stroke. Ischemia-reperfusion injury can also be generalized, e.g., in the case of resuscitation after hemorrhagic shock (Mazzone, A., et al., Leukocyte CD11/CD18 Integrins: Biological and Clinical Relevance, 80 *Haematologica* 161, 1995; see also, Reinhart W. H., Hemorheology: Blood Flow Hematology, 125 *Schweiz. Med. Wochenschr.* 387, 1995).

Ajoene is also a potent inhibitor of adhesive interactions for other cells, such as lymphoid cells. Adhesion of lymphocytes to each other and nonlymphoid cells is prerequisite to the development of any immune response, including adverse, undesirable, and self-destructive responses. Ajoene may, therefore, serve as an agent for the prevention, treatment, and control of various immunopathologies.

One group of such immunopathologies comprises diseases stemming from divers allergic reactions (e.g., delayed type hypersensitivity, Arthus reaction, and anaphylaxis). Allergy is an anomalous immune response to antigen challenge, characterized by recruitment of specific leukocyte subsets (e.g., cytotoxic lymphocytes and/or eosinophils) to the tissue, resulting in inflammation. Development of allergic inflammation is the main component in the pathogenesis of many diseases and illnesses, including, e.g., asthma, eczema, purpura pigmentosa chronica, various vasculitides, and hay fever, in addition to those mentioned above. Ajoene serves to control these diseases and illnesses.

Allograft rejection is another example of an undesirable immune response, in which the transplanted organ is recognized by the immune system as a foreign body ("nonself") and attacked in sequence by cytotoxic lymphocytes and phagocytes recruited from the circulation (in a manner similar to that described for reperfusion, supra). This inflammatory response results in progressive disruption of the tissue and graft necrosis. Ajoene may be used to prevent cell recruitment into transplanted tissue and thereby prolong graft survival.

Moreover, the transplanted organ also contains lymphocytes, which, in turn, recognize their new environment as "non-self." The immune response initiated by these donor lymphocytes in the body of the recipient produces a condition known as graft-versus-host disease (GVHD), which can lead to injury, both acute and chronic. Ajoene shows a significant potential in controlling both acute and chronic GVHD.

Self-destructive responses are caused by the failure of the immune system to distinguish "self" from "non-self." This group of immunopathologies comprises a wide variety of diseases (herein termed collectively "autoimmune diseases"), including, without limitation, rheumatoid arthritis, systemic lupus erythematosus, Sjögren's syndrome, multiple sclerosis, insulin-dependent diabetes mellitus, crescentic glomerulonephritis, Graves disease, Hashimoto's thyroiditis, and vasculitides. Other conditions and diseases may also fall into this category (see, e.g., the discussion of psoriasis, p. 16, infra). In spite of pronounced differences in the clinical picture of the various autoimmune diseases, the underlying mechanisms involve, in every case, recruitment of leukocytes to organs/tissues affected, resulting in destructive inflammation. Ajoene can be used to reduce or prevent this inflammation and thereby suppress the abnormal immune response. Accordingly, ajoene may be used to treat autoimmune diseases.

The beneficial effects of Ajoene are achieved because Ajoene is a modulating agent for integrins. As used herein, "modulate" means to affect the ability of a particular integrin to perform any of its functions. A modulating agent may act on an integrin directly, e.g., by binding to a portion of at least one subunit ($\alpha$ or $\beta$) of the integrin. The agent may also act in some other fashion that is not considered direct, e.g., through any of the various cellular substances and structures which ordinarily interact with or enable the target integrin. These substances and structures include, without limitation, transmembrane proteins (e.g., integrins themselves and integrin-associated proteins), membrane phospholipids, intracellular molecules with messenger-like function (e.g., integrin-modulating factor), enzymes, and regulatory and signaling proteins. Thus, for example, a modulation may result from alteration in integrin conformation, disassociation of the $\alpha$ and $\beta$ integrin subunits (or any of the parts thereof), disassociation of integrin clusters (and of clusters formed by integrins with other proteins), or from the loss of integrin-cytoskeleton connections, although modulation may also occur from other types of effects. The functions of integrins, as defined herein, are interrelated and include, inter alia, signaling, adhesion, fusion, and internalization.

As a result of its ability to modulate integrins, Ajoene can be used to treat any disease or condition that involves an integrin-mediated function as a mechanism, including those described above. For instance, Ajoene can be used to inhibit virus-cell fusion or undesired cell-cell fusion. Undesired cell-cell fusion can include cell-cell fusion (transitory or permanent) that results in the transfer of viral genetic material and cell-cell fusion that results in the formation of multinucleate cells (e.g., syncytia, giant cells, and osteoclasts). It can also include undesired fertilization of eggs by sperm and the formation of multinucleate germinal cells (syncytiotrophoblast). Thus, Ajoene can be used as a contraceptive, being administered per vaginas (topically), per os, or in any other appropriate way, when used for this purpose.

Ajoene also prevents conception at the stage of embryo implantation. For example, it can prevent the initial adhesion of the blastocyst to the endometrium and the migration of cytotrophoblasts through the maternal epithelium (i.e., processes similar to certain steps in the leukocyte extravasation cascade). Furthermore, Ajoene is capable of inhibiting cytotrophoblast invasion, a process differing from extravasation in that it goes from the tissues to the vascular lumen and that the invading cells cross the blood-tissue barrier from outside of the vessel. For example, the production of proteolytic enzymes that are used by cytotrophoblasts to penetrate the basement membrane is governed by integrin outside-in signaling. Modulation of the signaling function of integrins by Ajoene can either completely prevent the production of the requisite enzymes or attenuate it to an extent precluding invasion. Thus, Ajoene can be used as an effective emergency contraceptive to prevent unwanted pregnancy or interrupt it at an early stage.

There are yet other mechanisms whereby Ajoene can exert contraceptive effects. For example, it can prevent the chemotactic response of sperm in the vaginal environment (a specific case of cell homing) and sperm interactions with the epithelium of the female genital tract. Moreover, when administered to males, Ajoene can modulate integrins in sperm precursors and other testicular or epididymal cells, thereby interfering with the maturation processes and resulting in the production of fertilization-incompetent gametes or inhibition of fertilization-competent gametes.

The development of major bone diseases, including osteoporosis, is underlain by excessive bone resorption. This fundamental function is performed by osteoclasts. Osteoclasts are unique multinucleate bone cells formed by fusion of mononuclear progenitors called preosteoclasts. The regulation of osteoclast formation may be achieved by agents acting at various levels of osteoclast formation, including preosteoclast fusion (Zaidi, et al., Cellular Biology of Bone Resorption, 68 *Biol. Rev.* 197, 1993). Ajoene can regulate bone resorption because it can inhibit the fusion of preosteoclasts necessary for the formation of osteoclasts.

Granulomas are characteristic of chronic inflammatory lesions, such as those found in tuberculosis and other chronic infections. Granulomas are also present in sarcoidosis, a chronic, systemic inflammatory disease of unknown etiology. Granulomas present in cases of chronic infection and in sarcoidosis contain a large number of multinucleate giant cells formed by the fusion of macrophages. Other diseases associated with the formation of multinucleate cells include, without limitation, Crohn's disease, Langerhans cell histiocytosis, and giant cell arteritis. Ajoene can be used to inhibit the formation of these giant multinucleate cells with beneficial therapeutic effects.

Excessive formation of fibrous interstitial tissue (i.e., fibrosis, or sclerosis) is characteristic of certain diseases (such as scleroderma and idiopathic pulmonary fibrosis) and an outcome of chronic inflammatory processes (e.g., glomerular fibrosis). The development of fibrotic lesions and progression of fibrosis, associated with these conditions, diseases, and illnesses, has been linked to abnormal integrin expression and altered cell adhesion patterns. Ajoene can, therefore, be used for treatment of fibrotic lesions.

Lesions observed in skin diseases and illnesses of diverse origin, such as lichen planus, urticaria, dermatofibroma, psoriasiform dermatitides, and keratoses, are characterized by aberrant integrin expression. Ajoene can serve as an agent for the symptomatic treatment of these diseases, being administered topically, intradermally, and subcutaneously at the site of lesions, or in any other appropriate way, when used for this purpose.

Another disease characterized by the formation of cutaneous lesions is psoriasis. Although the etiology of psoriasis remains to be elucidated, its pathogenesis involves abnormal expression of integrins in target tissue (e.g., in vascular cells, keratinocytes, and dendritic cells), proliferation of endothelial and epidermal cells, and an autoimmune component (recruitment of lymphocytes and macrophages to skin and joints). Ajoene, therefore, can be used to treat psoriasis in multiple respects.

As a result of its antiviral and anti-inflammatory activity, Ajoene is likely to exhibit significant potency in the prevention and treatment of certain diseases with combined etiopathogenesis. As roughly elaborated herein, the term "etiopathogenesis" is used in reference to diseases for which no distinction can be drawn thus far as to the etiology and pathogenesis. One of such diseases is atherosclerosis. Atherosclerosis appears to be associated with a particular type of cytomegalovirus infection characterized by plaque formation along the blood vessels (Melnick, J. L., et al., Cytomegalovirus and Atherosclerosis, 17 BioEssays 899, 1995). A prominent feature of atherosclerosis is the recruitment of monocyte-macrophages into atherosclerotic plaques, which is an integrin-dependent process. Also, proliferation of smooth muscle cells, which contributes to the formation of atherosclerotic lesions, is regulated by integrins. As indicated elsewhere in this document, Ajoene inhibits the transmission of viral infections virus-to-cell and cell-to-cell. Integrin-mediated adhesion and signaling are also inhibited by Ajoene. Thus, Ajoene, for multiple reasons, can be used to treat diseases involving combinations of integrin-dependent etiopathogenetic factors, including atherosclerosis, both in humans and in other species.

Certain neurodegenerative disorders of unclear etiology, e.g., Alzheimer's disease and lateral amyotrophic sclerosis, involve autoimmune inflammation of nervous tissue as a pathogenetic mechanism. Ajoene should, therefore, demonstrate significant potency in mitigating the symptoms of these diseases and slowing down their progression. In particular, studies have shown that other anti-inflammatory treatments benefit Alzheimer's patients (McGeer, P. L., et al., The Inflammatory Response System of Brain: Implications for Therapy of Alzheimer's and Other Neurodegenerative Diseases, 21 Brain Res. Brain Res. Rev. 195, 1995; Breitner, J. C., et al., Delayed Onset of Alzheimer's Disease with Nonsteroidal Anti-Inflammatory and Histamine H2 Blocking Drugs, 16 Neurobiol. Aging 523, 1995).

To treat any one of these conditions, an effective amount of Ajoene is administered. Effective dosage forms, modes of administration, and dosage amounts may be determined empirically, and making such determinations is within the skill of the art. It is understood by those skilled in the art that the dosage amount will vary with the disease or condition to be treated, the severity of the disease or other condition, which integrin(s) is (are) to be modulated, the route of administration, the rate of excretion, the duration of the treatment, the identity of any other drugs being administered, the age, size and species of the animal, and like factors well known in the medical and veterinary arts. In general, a suitable daily dose of Ajoene will be that amount of the compound which is the lowest dose effective to produce a therapeutic effect. A suggested range of doses is from about 50 nanomoles to about 200 micromoles per liter. However, the total daily dosage will be determined by an attending physician or veterinarian within the scope of sound medical judgment. If desired, the effective daily dose of Ajoene may be administered as two, three, four, five, six or more sub-doses, administered separately at appropriate intervals throughout the day.

Ajoene may be administered in any desired and effective manner: as a pharmaceutical preparation for oral ingestion, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. For instance, the topical application of Ajoene to mucous membranes (in the form of creams, gels, suppositories, and other known means of topical administration) can be used to prevent HIV infection of mucosal cells, an important route of HIV transmission. In addition, intralymphatic administration of Ajoene may be advantageous in preventing the spread of HIV within the body. Further, Ajoene may be administered in conjunction with other antiviral drugs, other contraceptives, and other anti-shock or anti-inflammatory drugs or treatments. The Ajoene may be encapsulated or otherwise protected against gastric or other secretions, if desired.

Other modulating agents for cell integrin receptors exhibit similar benefits as Ajoene. Preferred are non-antibody modulating agents for integrins. Particularly preferred are small (low molecular weight), non-antibody modulating agents which are distinct from oligopeptide fragments of integrin ligands (e.g., ECM proteins, such as fibrinogen and fibronectin) and cyclic derivatives of these fragments.

In particular, disintegrins, and variants and analogs thereof, can be used. Disintegrins are a family of naturally-occurring cysteine-rich peptides originally isolated from viper venom, but also found on cells and elsewhere, many of which contain the sequence Arg Gly Asp (RGD) as an integrin recognition site. Disintegrins are defined by their specific amino acid sequences and three-dimensional structures. "Variants" of disintegrins are disintegrins engineered to have one or more amino acids added, deleted or replaced. "Analogs" are non-peptide mimetics of disintegrins or their variants. Disintegrins and variants thereof, their preparation and properties, are described in numerous publications, as are means of identifying analogs of disintegrins. See, e.g., Sato, et al., 111 J. Cell Biol. 1713, 1990; Rucinski, et al., 1054 Biochim. Biophys. Acta 257, 1990; Gould, et al., 195 Proc. Soc. Exp. Biol. Med. 168, 1990; Kini, et al., 28 Toxicon 1387, 1990; Soszka, et al., 196 Exp. Cell Res. 6, 1991; Calvete, et al., 30 Biochemistry 5225, 1991; Scarborough, et al., 266 J. Biol. Chem. 9359, 1991; Adler, et al., 31 Biochemistry 1031, 1992; Scarborough, et al., 268 J. Biol. Chem. 1058, 1993; Scarborough, et al. 268 J. Biol. Chem. 1066, 1993; Omori-Satoh, et al., 24 Toxicon 1045, 1986; Huang, et al., 262 J. Biol. Chem. 16157, 1987; Knudsen, et al., 179 Exp. Cell Res. 42, 1988; Gan, et al., 263 J. Biol. Chem. 19827, 1988; Huang, et al., 28 Biochemistry 661, 1989; Garsky, et al., 86 Proc. Natl. Acad. Sci. U.S.A. 4022, 1989; Shebuski, et al., 264 J. Biol. Chem. 21550, 1989; Chao, et al., 86 Proc. Natl. Acad. Sci. U.S.A. 8050, 1989; Musial, et al., 82 Circulation 261, 1990; Williams, et al., 1039 Biochim. Biophys. Acta 81, 1990; Savage, et al., 265 J. Biol. Chem. 11766, 1990; Takeya, et al., 265 J. Biol. Chem. 16068, 1990; Neeper, et al., 18 Nucl. Acids Res. 4255, 1990; Seymour, et al., 265 J. Biol. Chem. 10143, 1990; Shebuski, et al., 82 Circulation 169, 1990); Dennis, et al., 87 Proc. Natl. Acad. Sci. U.S.A. 2471, 1990; Mazur, et al., 202 Eur. J. Biochem. 1073, 1991; Saudek, et al., 202 Eur. J. Biochem. 329, 1991; Huang, et al., 109 J. Biochem. 328, 1991; Adler, et al., 253 Science 445, 1991; Saudek, et al., 30 Biochemistry 7369, 1991; Huang, et al., 1074 Biochim. Biophys. Acta 144, 1991; Huang, et al., 1074 Biochim. Biophys. Acta 136, 1991; Huang, et al., 277 Biochem J. 351, 1991; Huang, et al., 42 Biochem. Pharmacol. 1209, 1991; Yamakawa, et al., 109 J. Biochem., 667, 1991; Dalvit, et al., 202 Eur. J. Biochem. 315, 1991; Cooke, et al., 202 Eur. J. Biochem. 323, 1991; Au, et al., 181 Biochem. Biophys. Res. Commun. 585, 1991; Chen,, et al., 30 Biochemistry 11625, 1991; Kini, et al., 30 Toxicon 265, 1992; Hite,, et al., 31 Biochemistry 6203, 1992; Calvete, et al., 309 FEBS Letters 316, 1992; Sheu, et al., 83 Jpn. J. Cancer Res. 885, 1992; Paine, et al., 267 J. Biol. Chem. 22869, 1992; Takeya, et al., 267 J. Biol. Chem.

14109, 1992; Chang, et al., 190 *Biochem. Biophys. Res. Commun.* 242, 1993; Takeya, et al., 113 *J. Biochem.* 473, 1993; Adler, et al., 32 *Biochemistry,* 282, 1993; Dennis, et al., 15 *Proteins: Structure. Function and Genetics* 312, 1993; Hite, et al., 308 *Arch. Biochem. Biophys.* 182, 1994.

The disintegrins, and variants and analogs thereof, like Ajoene, can be used to treat viral infections, shock, and inflammation, to inhibit fertilization of eggs by sperm, to suppress immune responses, to treat arthritis and autoimmune diseases, to prevent undesired integrin-mediated cell-cell fusion, and to treat other diseases and conditions against which Ajoene is effective. The disintegrins and variants and analogs thereof may be used for these purposes as described herein for Ajoene. In particular, effective dosage forms, modes of administration and dosage amounts for administration of disintegrins, and variants and analogs thereof, to patients may be determined empirically as described herein for Ajoene, and making such determinations is within the skill of the art. A suggested range of doses is 10 to 5000 nanomoles per liter blood plasma, depending on the condition to be treated, on which disintegrin (or disintegrin analog or variant) is to be used, which integrin(s) is (are) intended to be modulated, and on other pertinent factors, as herein discussed. However, appropriate doses may be derived for any particular condition and mode of administration, based on the relative potency exhibited by Ajoene and disintegrins (or variants or analogs of disintegrin in question) under comparable experimental conditions.

Other suitable integrin modulating agents for use in practice of the invention may be identified by their ability to interfere with integrin-mediated functions. As noted above, fundamental integrin-mediated functions include cell signaling, cell adhesion, cell fusion, and internalization. Simple in vitro screening assays can be used to ascertain if compounds inhibit such integrin-mediated functions. Suitable assays are described in the examples and others are well-known in the art. For instance, in vitro induced platelet aggregation, which is routinely performed in any clinical laboratory, provides a particularly well-known example of a system that allows to detect and measure integrin signaling (inside-out) and integrin-mediated adhesion (see, e.g., Huang, T.-F., et al., Mechanism of Action of the Antiplatelet Peptide, Arietin, from *Bitis arietans* Venom, 1074 *Biochim. Biophys. Acta* 144, 1991). Analogous screening systems for neutrophil integrins have been described (see, e.g., Hoffstein, S. T., et al., Degranulation, Membrane Addition, and Shape Change During Chemotactic Factor-Induced Aggregation of Human Neutrophils, 95 *J. Cell Biol.* 34, 1982). Similar assays exist for integrin-mediated fusion (Bronson, R. A., et al., Evidence that an Arg-Gly-Asp Adhesion Sequence Plays a Role in Mammalian Fertilization, 43 *Biol. Reprod.* 1019, 1990), integrin-mediated outside-in signaling (see, e.g., Shattock, R. J., et al., Cellular Adherence Enhances HIV Replication in Monocytic Cells, 145 *Res. Virol.* 139, 1995), and integrin-mediated internalization (see, e.g., Handagama, P., et al., supra; compare, e.g., Wencel-Drake, J. D., et al. Arg-Gly-Asp-dependent Occupancy of GPIIb/IIIa by Applagin: Evidence for Internalization and Cycling of a Platelet Integrin, 81 *Blood* 62, 1993, demonstrating the existence of a separate, signal-independent GPIIb/IIIa internalization pathway).

Finally, the invention provides a method of treating a tissue by contacting the tissue with an integrin modulating agent. Such treatment improves the condition of the tissue for subsequent use, as compared to tissue which is not treated with an integrin modulating agent. In particular, tissue which is to be transplanted into a recipient may be treated with an integrin modulating agent, and the chances of the tissue being successfully transplanted will be increased.

The tissue to be treated may be any tissue. For instance, the tissue may be an organ (such as a heart, blood vessel, lung, liver, kidney, skin, cornea, or part of an organ, such as a heart valve), or a non-organ tissue (such as bone marrow, stem cells, or gametes). The tissue is treated by contacting it one or more times with an effective amount of an integrin modulating agent. Methods of contacting tissues with agents are well known in the art. For instance, the contacting can be accomplished conveniently by rinsing or perfusing the tissue with, or submersing the tissue in, a solution of the integrin modulating agent in a physiologically acceptable diluent. Physiologically-acceptable diluents are those that are compatible with, and not harmful to, the integrin modulating agent and the tissue. Such diluents are well known and include saline and other salt solutions.

Effective amounts of the integrin modulating agent may be determined empirically, and making such determinations is within the skill of the art. It is understood by those skilled in the art that the amount may vary as a result of one or more factors, including the type and size of the tissue, the intended use of the tissue, the length of storage of the tissue before use, the identity of any other agents being used, the number of treatments, and like factors well known in the art.

The integrin modulating agent may be used in conjunction with other agents to treat tissue. For instance, the tissue may also be treated with preservation agents (i.e., agents which inhibit deterioration of the condition of the tissue), antibiotics, antifungal drugs, antiviral drugs, antiinflammatory drugs, or other treatments (e.g., lung surfactants in the case of lung tissue).

After being contacted with the integrin modulating agent, the tissue may be used immediately or may be stored until needed. Methods of storing tissue are well known in the art. The tissue may be stored in contact with the integrin modulating agent. Tissues are preferably stored at low temperatures, typically 4–18° C., and non-organ tissues may be frozen. The time of storage will vary depending on the type of tissue, the storage environment (including the temperature of storage), and the intended use. Such times can be determined empirically, and making such determinations is within the skill in the art. Regardless of the length and conditions of storage, treatment with an integrin modulating agent mitigates the effects of harvest and/or storage, and treated tissues will be in better condition than tissues not treated with an integrin modulating agent.

Tissues treated with integrin modulating agents may be used for a variety of purposes. For instance, they may be transplanted into recipients. They may also be used for research purposes, such as studying the function of the tissue.

The integrin modulating agents are those described above. Preferred integrin modulating agents are Ajoene, disintegrins, and analogs and variants thereof. Most preferred is Ajoene because Ajoene has beneficial and protective effects on tissue beyond those that can be attributed solely to its ability to modulate integrins. In particular, tissues treated with Ajoene appear healthier than tissue treated with other integrin modulating agents. What constitutes healthy tissue is well known in the art, and assessing the health of a tissue is within the skill in the art.

Treatment of a tissue with an integrin modulating agent improves the condition of the tissue by reducing the negative effects and consequences of harvesting and storing tissue. For instance, integrin modulating agents inhibit (prevent or reduce) the adhesion and aggregation of cells which would otherwise cause injury to a tissue (see the discussion above). Thus, treatment of a tissue with an integrin modulating agent prevents or reduces damage to the tissue.

In particular, ischemia (anemia due to constriction or obstruction of a blood vessel) occurs upon harvesting an organ. Both the injury due to ischemia and that due to reperfusion after ischemia (which generally occurs upon resuming blood flow in an organ, such that occurring when transplanting an organ into a recipient), can be inhibited by treatment of the organ with an integrin modulating agent. To achieve maximum inhibition of ischemic injury and ischemic reperfusion injury, the organ should be contacted with the integrin modulating agent immediately after harvesting of the organ to mitigate the rapid onset of injury and other changes associated with ischemic injury. Such treatment has beneficial effects even for organs that are to be used immediately, such as in the case of many transplants. Preferably the contacting takes place by perfusing the organ with a solution comprising the integrin modulating agent. For organs that are stored (even for a short time), benefits are obtained by contacting the organ with an integrin modulating agent immediately prior to use. This treatment may serve, among other purposes, to eliminate the effects of any cytokines that may have been produced, as well as to prevent adhesion and aggregation of cells which would otherwise cause tissue injury. The treatment of an organ after storage can be the first treatment of the organ with an integrin modulating agent, or can be the second treatment of an organ which was treated immediately after harvest. Again, the organ is preferably treated by perfusion with a solution comprising the integrin modulating agent.

As discussed above, integrin modulating agents suppress undesired immune responses. Thus, treatment of a tissue with an integrin modulating agent prior to transplantation acts as an initial treatment for the prevention of graft rejection and/or graft versus host disease (GVHD) in transplant recipients.

Of course, the recipient may receive additional amounts of an integrin modulating agent to prevent graft rejection and/or GVHD as described above. The amount administered to the recipient should also be chosen so that inhibition of injury due to ischemia and ischemia reperfusion is continued.

Finally, integrin modulating agents can inhibit the transmission of viral infections from a tissue to a recipient of transplanted tissue and vice versa (see the discussion above). This includes all of the viral infections described above.

The above disclosure and the examples below are for illustrative purposes only, and are not intended to limit the invention of this application, which is as defined in the claims below.

EXAMPLES

Example 1

Ajoene Affects Cellular Activities Mediated by Several Distinct Integrin Receptors Platelet aggregation was measured turbidimetrically on a standard platelet aggregometer equipped with a recorder. Samples of platelet-rich plasma (PRP) were standardized with respect to the cell density ($3 \times 10^8$ per ml); maximal light transmission (LT) was calibrated with platelet-poor plasma (PPP). Aliquots of PRP (0.25 ml in glass cuvettes) were stirred in the cell of the device (1000 rpm, 37° C.) with Ajoene (0–100 micromoles per liter final concentration) for 1 min., followed by addition of the aggregation stimuli. (Unless specified otherwise, all the experiments described in this Application were performed with Ajoene that represented a 1:1 mixture of E- and Z-stereoisomers.) LT increments were traced for 5 min. Maximal rate of aggregation was derived from the slope of each curve; $IC_{50}$ for Ajoene was determined by a method such as that described in Vrzheshch, et al., Cell Response Kinetics: the Phenomenon of Supercooperativity in Aggregation of Human Platelets, 66 *Thrombos. Res.* 537, 1992.

Neutrophil aggregation was assayed as described above for the platelet system, with some modifications. Freshly isolated neutrophils were finally suspended in a buffer (120 mM NaCl, 4 mM KCl, 10 mM dextrose, 2 mM $CaCl_2 \cdot 2H_2O$, 2 mM $MgCl_2 \cdot 6H_2O$, and 20 mM Tris; pH 7.4) to the final density of $10^7$ cells per ml. Aliquots of neutrophil suspension (0.25 ml in siliconized glass cuvettes; $10^7$ cells per ml) were stirred in the cell of the aggregometer with 5 micrograms per ml cytochalasin B (1000 rpm, 37° C.) for 1 min. Ajoene (0–50 micromoles per liter) and N-formyl-L-methionyl-L-leucyl-L-phenylalanine ($10^{-7}$ M) were then introduced into the suspension sequentially, with an interval of 1 min. Maximum LT (100%) was calibrated with the same buffer.

T-lymphocytic H9 and Jurkat cells were maintained as suspension cultures in RPMI-1640 medium supplemented with 10% (v/v) heat-inactivated fetal calf serum, 50 micrograms/ml gentamycin and 2 mM L-glutamine. To assess the effects of Ajoene on adhesive interactions of the cells, H9 cells or Jurkat cells were seeded in 96-well flat-bottomed plates ($3 \times 10^5$ cells per well) and cultured in the presence of log 10 dilutions of Ajoene (experiment) or its vehicle (control) for 16 to 24 h.

Ajoene inhibited platelet aggregation in PRP with an $IC_{50}$ of about 50 micromoles per liter. Ajoene blocked N-formyl-L-methionyl-L-leucyl-L-phenylalanine-stimulated neutrophil aggregation ($IC_{100}$ of about 10 micromoles per liter) and caused rapid deaggregation when added to aggregated neutrophils. The clusters normally formed by H9 cells and Jurkat cells in culture were disrupted by Ajoene with an $IC_{50}$ of about 50 nanomoles per liter for each cell system.

The requirement of integrins for the formation of cell-to-cell contacts in each of these systems has long been established. It is known that in platelets the relevant integrin is GP IIb/IIIa ($\beta 3$). Neutrophil aggregation is underlain by interactions of $\beta 2$ integrins (e.g., LFA-1 and/or Mac-1) with their surface counterstructures, while cohesion of T-cells is supported by both $\beta 2$ integrins and fibronectin-binding $\beta 1$ integrins (e.g., VLA-4 and VLA-5). Hence, Ajoene is capable of modulating integrin receptors of at least three distinct subfamilies ($\beta 1$, $\beta 2$, and $\beta 3$).

This example also demonstrates that Ajoene affects at least two integrin functions: inside-out signaling (upregulation of integrins upon platelet and neutrophil activation) and adhesion.

Example 2

Integrin-Modulating Properties of Ajoene are not Stereospecific

Synthetic stereoisomers of Ajoene exhibited equal anti-aggregatory activity ($IC_{50}$ of about 50 micromolar concentration of Ajoene for platelets, $IC_{100}$ of about 10 micromolar concentration of Ajoene for neutrophils).

Example 3

Ability Of Ajoene To Modulate Adhesion of Cells to Substrata, Mediated by VLA-4

Microtiter plates were coated with ligands of the integrin VLA-4, i.e., recombinant human VCAM-1 (500 nanograms per well) or the fragment of connective segment of human fibronectin (CS-1), covalently attached to ovalbumin (5 micrograms per well) by overnight incubation (4° C.) with solutions of the proteins in phosphate-buffered saline (PBS). The plates were blocked with 1% bovine serum albumin (BSA) in Hanks' buffered salt solution (HBSS-BSA). The cells (Jurkat or human melanoma MV3) were labeled with the fluorescent dye 5-chloromethylfluorescein diacetate (CMFDA) and introduced into the wells of the plates ($10^5$ cells per well) together with varying amounts of Ajoene. After incubation at 37° C. for 1 h, the unbound cells were removed by aspiration and the wells washed four times with HBSS-BSA. Thereafter, the bound cells were lysed with 0.5% Triton X-100, and the fluorescence was measured using a Cytofluor 2300 plate reader. The number of adherent cells was calculated from a standard dilution curve of Triton X-100 lysates of the CMFDA-labeled cells.

Ajoene inhibited VLA-4-dependent adhesion of Jurkat and MV3 cells to VCAM-1 with $IC_{50}$ values of 250 and 125 micromoles per liter, respectively. However, no inhibition of adhesion to CS-1 could be detected in this concentration range. Therefore, the CS-1 recognition site of VLA-4 was more resistant to modulation with Ajoene than the VCAM-1 recognition site.

Because there is no way for the cells tested to adhere to the substrata otherwise than via VIA-4, this example provides conclusive evidence that Ajoene modulates VLA-4 and affects its adhesion function.

Example 4

Ability of Ajoene to Modulate LFA-1-mediated Homotypic Adhesion and Inside-out Signaling Normal human peripheral blood leukocytes (PBLS) were cultured for 5 days without stimulation in complete RPMI medium (Sigma Chemical Co., St. Louis, Mo.), washed, and resuspended at $9 \times 10^6$ cells/ml in the same medium. Fifty microliters of the cells were added in duplicate to wells containing 100 microliters of an Ajoene solution (50 micrograms/ml), anti-LFA-1 antibody (H52) solution (20 micrograms/ml), or vehicle controls. The plate was then incubated for 30 min at 37° C. before adding to each well 50 microliters of a solution of 12-O-tetradecanoyl 4-β-phorbol 13-acetate (TPA) to the final concentration of 125 ng/ml). The plate was incubated for 45 min at 37° C., followed by additional 10-min incubation at room temperature on a shaking platform. The cells were allowed to settle, and adhesion was quantitated by counting the number of free cells in random high-power fields in the duplicate wells. Following incubation with TPA, 75 to 90% of cells are typically found in large aggregates as a result of LFA-1 upregulation. TPA induced a 90% aggregation in PBLs that were preincubated with vehicle controls. The aggregatory response was completely inhibited by H52, the monoclonal antibody used as a positive control, indicating that the aggregatory response was mediated by LFA-1. Pretreatment with Ajoene at ~100 micromoles per liter concentration completely inhibited the TPA-induced homotypic adhesion of PBLs. This example provides conclusive evidence that, in addition to GP IIb/IIIa and VIA-4, Ajoene modulates the integrin LFA-1. In addition, because TPA-induced homotypic aggregation of PBLs involves LFA-1 upregulation (inside-out signaling), the above result further confirms that modulation of LFA-1 with Ajoene affects both the signaling and adhesion function of this integrin.

Example 5

Ajoene Modulates VLA-4- and LFA-1-mediated Heterotypic Cell Adhesion and Inside-out Signaling SVT2 cells transfected with human ICAM-1 or VCAM-1 (SVT2/ICAM-1 and SVT2/VCAM-2, respectively) were plated into 96-well plates and cultured overnight. (SVT2/ICAN-1 and SVT2/VCAM-2 were demonstrated previously to express ICAM-1 and VCAM-1, respectively, on their surface.) Jurkat cells were washed and cultured overnight in the presence of 100 microCurie/ml of $Na_2^{51}CrO_4$. The labeled Jurkat cells were washed three times and resuspended at a density of $4 \times 10^6$ cells/ml in complete RPMI medium. Serial dilutions of Ajoene were prepared in complete RPMI medium. Aliquots of the cells (0.5 ml) were then mixed with an equal volume of Ajoene dilutions (1:1 v/v), and the mixtures incubated at 37° C. for 30 min. Thereafter, Ajoene-incubated cells were added in duplicate to SVT2/ICAM-1 and SVT2/VCAM-1 monolayers, and TPA was introduced into each well to the final concentration of 125 ng/ml. The plates were incubated at 37° C. for 45 min, after which the non-adherent cells were removed by washing with warm complete RPMI medium. The bound labeled cells were lysed by adding 1% Triton X-100 solution in 0.1 N HCl. The lysates were assayed in a gamma counter to determine the percentage of bound cells. Because SVT2 cells do not contain the ligands for LFA-1 and VLA-4, adhesion to Jurkat cells becomes possible only after transfection of SVT2 cells with ICAM-1 or VCAM-1. Thus, coculturing of Jurkat cells with SVT2/ICAM-1 and SVT2/VCAM-1 cells makes it possible to assess, respectively, the function of IFA-1 and VLA-4 under identical conditions. In the absence of TPA, 10 and 20% of the added Jurkat cells adhered to SVT2/ICAM-1 and SVT2/VCAM-1 cells, respectively. Activation of Jurkat cells by TPA and the resulting upregulation of LFA-1 and VLA-4 (inside-out signaling) invariably produced adhesion levels in excess of 90% in both experimental settings. Ajoene inhibited adhesion of activated Jurkat cells to SVT2/ICAM-1 and SVT2/VCAM-1 monolayers with $IC_{50}$ values of 10 micromoles per liter and ~20 micromoles per liter, respectively. This difference in the relative potency of inhibition was statistically significant, indicating that LFA-1 is slightly more sensitive to Ajoene than VLA-4. This example demonstrates that Ajoene modulates LFA-1 and VLA-4 and impairs the inside-out signaling and adhesion functions of these integrins.

Example 6

In Vivo Modulation by Ajoene of LFA-1 and VLA-4-mediated Recruitment of Monocytes and Neutrophils into Inflamed Joints Rat adjuvant arthritis is characterized by integrin-mediated migration of $^{51}Cr$-labeled monocytes and $^{111}In$-labeled neutrophils into the inflamed synovium, which attains maximum between days 14 and 21 after the immunization. This model of human rheumatoid arthritis was used to assess in vivo effects of Ajoene on integrins that are known to be modulated by Ajoene in vitro.

Adjuvant arthritis was induced in 6–8 week old inbred male Lewis rats by immunization on the lower back with 0.5 mg *Mycobacterium butyricum* (Difco Laboratories, Inc., Detroit, Mich.) in 0.05 ml mineral oil in two sites subcutaneously at the base of the tail. All the animals developed polyarticular arthritis between days 11 and 13 after immunization. For clinical scoring, 0–4 points were assigned per limb and tail, based on the severity of erythema, swelling, and limitation of movement (the maximal possible score was 20).

Rat blood monocytes and neutrophils for migration studies were obtained by the hydroxyethyl starch (HES) exchange transfusion technique. The total blood volume of a donor rat was exchanged using 50 ml 6% HES solution in saline (DuPont Chemical Co., Dorval, Canada). After recovery of 40–45 ml blood/HES perfusate, the red cells were allowed to sediment (1 g) and the leukocyte-rich plasma was harvested. The leukocytes were recovered by centrifugation, resuspended in calcium-magnesium-free Tyrode's solution supplemented with 10% platelet-poor plasma (TS-PPP), and centrifuged in a discontinuous 63%/74% gradient of isotonic Percoll (Pharmacia Fine Chemicals, Dorval, Canada). The top layer, containing mononuclear cells (MN), and the cells in the 63%/74% interface, containing neutrophils, were collected, washed, and resuspended in TS-PPP. To obtain purified monocytes, the osmolality of the MN suspension was increased by adding 9% NaCl, and the suspension was centrifuged in a 40%/55%/58% Percoll gradient; monocytes were harvested at 40%/55% and 55/158% interfaces, washed, and resuspended in TS-PPP.

Thereafter, monocytes ($10^7$ cells/ml) were labeled with 75 microCurie/ml of $Na_2{}^{51}CrO_4$ (Amersham, Oakville, Canada) at 37° C. for 30 min. Neutrophils ($10^7$ cells/ml) were labeled with 1 microCurie/ml of $^{111}$In oxine (Amersham) for 10 min. Both populations were washed to remove excess labeled material and checked for viability and purity. The viability of either cell population used in the experiments was in excess of 95% (as double-checked by Trypan blue exclusion and neutral red staining). The separation procedure described above ordinarily produced populations that contained no less than 90% monocytes and no less than 95% neutrophils.

Ajoene was administered to anaesthetized arthritic rats intravenously (50 mg/kg per rat; infusion rate, 5 mg/min), as a suspension in Intralipid, a parenteral nutritive containing fractionated soybean oil (200 g/l), fractionated egg phospholipids (12 g/l), and glycerol (22 g/l). To prepare this suspension, Ajoene was first dissolved in ethanol to the concentration of 2 moles per liter. This solution was then introduced under vigorous stirring into Intralipid (KabiVitrum; Stockholm, Sweden) to the final concentration of 0.085 moles per liter (20 mg/ml) Ajoene; the content of ethanol in the suspension thus obtained did not exceed 3% (v/v). Control arthritic rats received, under the same experimental conditions, adequate volumes of the vehicle (Intralipid supplemented with 3% ethanol v/v). All subsequent manipulations with animals of both groups were identical; on the day of the experiment, mean scores in control and treatment rats were 12.5 and 14.0, respectively.

Within 2–3 min of Ajoene administration, each rat was injected intravenously with $^{51}$Cr-labeled monocytes ($4–6\times10^6$ monocytes, carrying $1.0–1.5\times10^5$ cpm $^{51}$Cr) and $^{111}$In-labeled neutrophils ($10^7$ neutrophils, carrying $2–5\times10^5$ cpm $^{111}$In). After 2 h, 1 ml of blood was collected from each rat (for differential leukocyte counts and plasma $^{51}$cr) and the animals were sacrificed. The hindlimbs were sectioned just above and below the tibiotalar joint, providing tarsal and talar joint samples for gamma counting (model 1280 gamma spectrometer; LKB Instruments, Inc.; Gaithersburg, Md.). The activity of the tail was taken as a measure of the process in vertebral joints.

The results are summarized in the tables below.

TABLE 1

Inhibition by Ajoene of monocyte recruitment to inflamed joints

| Sample | Control | Ajoene | Significance |
|---|---|---|---|
| | Accumulation of $^{51}$Cr-labeled Monocytes, cpm per sample (mean ± SEM) | | |
| Talar joint | 42,304 ± 3,618 | 25,078 ± 2,872 | P < 0.006 |
| Tarsal joint | 16,604 ± 4,374 | 10,365 ± 2,572 | N.S. |
| Vertebral joints | 5,262 ± 1,400 | 2,737 ± 521 | P = 0.079 |

TABLE 2

Inhibition by Ajoene of neutrophil recruitment to inflamed joints

| Sample | Control | Ajoene | Significance |
|---|---|---|---|
| | Accumulation of $^{111}$In-labeled Neutrophils, cpm per sample (mean ± SEM) | | |
| Talar joint | 31,084 ± 1,940 | 15,052 ± 1,570 | P < 0.001 |
| Tarsal joint | 12,554 ± 2,534 | 7,353 ± 1,438 | P = 0.085 |
| Vertebral joints | 5,775 ± 782 | 3,658 ± 546 | P = 0.089 |

Treatment with Ajoene resulted in a highly significant, ~50% inhibition of monocyte (Table 1) and neutrophil (Table 2) recruitment to the talar joints, which are the most susceptible to inflammation in this model. Moreover, these joints yield consistent recruitment of monocytes and neutrophils, and, therefore, the values obtained are the most reliable. (The tarsal joints and vertebral spine joints are also affected by the inflammation, but the variability is greater, than in the case of talar joints, and, consequently, the effects of treatment with Ajoene are not as pronounced.)

Notably, blocking monoclonal antibodies (MABs) against VIA-4, LFA-1, or CR3 do not inhibit monocyte or neutrophil accumulation in the talar joints, when given alone. Only combined administration of antibodies against different integrins (e g., anti-LFA-1 plus anti-VLA-4 or anti-LFA-1 plus anti-Mac-1; see, Issekutz, A. C., et al., Monocyte Migration to Arthritis in the Rat Utilizes both CD11/CD18 and Very Late Activation Antigen 4 Integrin Mechanisms, 181 *J. Exp. Med.* 1197, 1995, and Issekutz, T. B., et al., Rat Blood Neutrophils Express Very Late Antigen 4 and It Mediates Migration to Arthritic Joint and Dermal Inflammation, 183 *J. Exp. Med.* 2175, 1996) produces an inhibition that is comparable in extent with that induced by Ajoene.

Thus, Ajoene exerts in vivo the same integrin-modulating effects as in vitro, i.e., it acts on several distinct integrins. In particular, this example demonstrates a pronounced in vivo effect on β2 integrins (e.g., LFA-1) and β1 integrins (eg., VLA-4), although modulation of other integrins cannot be ruled out.

In vivo inhibition by Ajoene of leukocyte recruitment in a model of rheumatoid arthritis indicates that Ajoene can be used to treat rheumatoid arthritis, as well as other autoimmune (e.g., lupus, diabetes, Sjögren's syndrome, and vasculitides) and inflammatory diseases (e.g., ischemia-reperfusion injury and graft rejection) characterized by integrin-mediated recruitment of leukocytes. Also, other types of cell migration, which are critical to the development of undesirable conditions, diseases, and illnesses (e.g., embryo implantation) will likewise be inhibited by Ajoene in vivo.

Example 7

In Vivo Modulation by Ajoene of LFA-1- and VLA-4-mediated Recruitment of Monocytes and Neutrophils into Inflamed Skin Chemotactic factors (e.g., $C5a_{desArg}$) and cytokines, such as tumor necrosis factor α (TNF) or interferon gamma (IFN), induce rapid cutaneous inflammatory reactions, when injected intradermally. These inflammatory reactions are characterized by integrin-mediated migration of $^{51}$Cr-labeled monocytes and $^{111}$In-labeled neutrophils. The mechanisms of leukocyte recruitment to the inflammatory loci differ, however, in that chemotactic factors act primarily on leukocytes (by upregulating integrins), whereas TNF and IFN activate endothelial cells (which results, inter alia, in rapid expression of integrin ligands, such as ICAM-1 and VCAM-1).

Agents used for the induction of the inflammation included rat IFN, recombinant mouse TNF (Genentech, South San Francisco, Calif.), and Zymozan-activated serum (ZAS). ZAS, a source of $C5a_{desArg}$, was generated by activating complement in normal rat serum with 5 mg/ml of Zymozan A (Sigma Chemical Company, St. Louis, Mo.) at 37° C. for 60 min, after which the zymozan was removed.

Rat monocytes and neutrophils were isolated and labeled as described in Example 6, supra. Male Lewis rats were administered intravenously with 50 mg/kg Ajoene (treatment group) or its vehicle (control), followed within 2–3 min by infusion of the labeled cells. Immediately afterwards, the skin on the back of all animals was shaved and the inflammatory stimuli and the diluent control were injected intradermally at several sites of the skin of each animal. Two hours later, 1 ml of blood was taken from each rat, and the animals were sacrificed. The dorsal skin, including the area of dermal inflammatory reactions, was removed and frozen, and the injected skin sites were punched out with a 12-mm punch and counted in a gamma spectrometer (model 1280, LXB Instruments).

TABLE 3

Inhibition by Ajoene of monocyte recruitment to inflamed skin

| Inflammatory stimulus | Accumulation of $^{51}$Cr-labeled Monocytes, cpm per inflammatory locus (mean ± SEM) | | Significance |
|---|---|---|---|
| | Control | Ajoene | |
| 50% ZAS | 2,550 ± 274 | 1,268 ± 170 | P < 0.002 |
| 25% ZAS | 1,557 ± 158 | 944 ± 127 | P < 0.020 |
| 10 ng TNF | 2,506 ± 70 | 1,274 ± 140 | P < 0.002 |

TABLE 3-continued

Inhibition by Ajoene of monocyte recruitment to inflamed skin

| Inflammatory stimulus | Accumulation of $^{51}$Cr-labeled Monocytes, cpm per inflammatory locus (mean ± SEM) | | Significance |
|---|---|---|---|
| | Control | Ajoene | |
| 300 U IFN | 1,747 ± 205 | 468 ± 64 | P < 0.001 |
| Diluent control | 82 ± 23 | 15 ± 10 | N.S. |

TABLE 4

Inhibition by Ajoene of neutrophil recruitment to inflamed skin

| Inflammatory stimulus | Accumulation of $^{111}$In-labeled Neutrophils, cpm per inflammatory locus (mean ± SEM) | | Significance |
|---|---|---|---|
| | Control | Ajoene | |
| 50% ZAS | 11,486 ± 776 | 7,926 ± 378 | P < 0.001 |
| 25% ZAS | 7,751 ± 280 | 5,558 ± 236 | P < 0.001 |
| 10 ng TNF | 1,750 ± 36 | 1,289 ± 84 | P < 0.006 |
| 300 U IFN | 223 ± 42 | 160 ± 11 | P < 0.060 |
| Diluent control | 62 ± 13 | 53 ± 8 | N.S. |

Treatment with Ajoene resulted in a highly significant inhibition of monocyte migration to loci of acute cutaneous inflammation (by 50–75%). In the case of neutrophils, the inhibition was less pronounced (by 30–40%), but also statistically significant. None of the anti-integrin MABs tested previously in the same model inhibited the cell recruitment to any significant degree, when administered alone. Only a combination of an anti-LFA-1 and an anti-VLA-4 MABs demonstrated the same degree of attenuation of monocyte/neutrophil accumulation at the loci of cutaneous inflammation as Ajoene.

This example provides further evidence that Ajoene modulates in vivo β2 and β1 integrins, e.g., LFA-1 and VIA-4, although effects on other integrins are also likely to occur. The in vivo integrin modulation by Ajoene results in significant inhibition of leukocyte recruitment to inflammatory loci and attenuation of inflammation. Notably, the anti-inflammatory activity of Ajoene shows essentially no dependence on the primary mechanism operative in the recruitment of leukocytes to the inflammatory loci (e.g., chemotactic stimulation of leukocytes vs. cytokine activation of the endothelium).

Thus, this example indicates that Ajoene can treat a broad range of inflammatory diseases, regardless of the particular mechanism of inflammation. More specifically, this example underscores the ability of Ajoene to treat various skin diseases and illnesses, such as psoriasis, scleroderma, eczema, and allergy.

When viewed together, Examples 6 and 7 provide significant evidence that in vivo modulation of integrins by Ajoene takes place in various locations of the body. Whatever organ or tissue is affected, Ajoene will modulate its target integrins in essentially the same way as it modulates them in vitro. Thus, Ajoene can treat diseases involving multiple locations or occurring systemically throughout the whole body (e.g., shock and generalized ischemia-reperfusion injury).

Example 8

Ajoene as an Inhibitor of Fusion Leading to Syncytium Formation in HIV-infected Cells Chronically infected and uninfected cell lines (HIV donors and targets, respectively) were maintained as suspension cultures in RPNI-1640 medium supplemented with 10% (v/v) heat-inactivated fetal calf serum, 50 micrograms/ml gentamycin and 2 mM L-glutamine. HIV donors used were (1) a cloned population of H9 cells harboring the genome of HIV-$1_{RF}$ (H$9_{RF}$ cells); and (2) a cloned population of SupT1 cells harboring the genome of HIV-$1_{LAV-BRU}$ (SupT$1_{LAV-BRU}$ cells). To assess the effect of Ajoene on syncytium formation, the donors were mixed with their respective recipients, H9 and SupT1, at a ratio of 1:2 in 96-well flat-bottomed plates ($3 \times 10^5$ cells per well). Log 10 dilutions of Ajoene were then introduced into the wells, and the cells were cocultured for 16 h. Control wells received the vehicle of Ajoene. By the end of the incubation period syncytia were counted, and the values of $IC_{50}$ for Ajoene were calculated by plotting relative amounts of syncytia (percent of the syncytia formed in the absence of the compound) against Ajoene concentration.

TABLE 5

| HIV donor | HIV recipient | $IC_{50}$ of Ajoene, nanomoles/l |
|---|---|---|
| H$9_{RF}$ | H9 | ~50 |
| SuPT$1_{LAV-BRU}$ | SupT1 | ~5 |

Specifically, Ajoene inhibited the fusion of uninfected cells with HIV-infected cells and the formation of syncytia, resulting from this fusion, with $IC_{50}$ values in the range from 5 to 50 nanomoles per liter Ajoene concentration at 16 h incubation. The fusion machinery of cells operative in the formation of syncytia in HIV infection involves as components $\beta 1$ and $\beta 2$ integrins (e.g., VLA-3 and LFA-1). Thus, this example demonstrates that modulation by Ajoene of $\beta 1$ and $\beta 2$ integrins affects yet another fundamental integrin function, fusion.

Taken together with the examples provided supra, this example provides conclusive evidence that Ajoene will inhibit the formation of syncytia associated with HIV infection in patients. Furthermore, fusion events associated with other viral infections, noninfectious diseases (e.g., granulomatous inflammations and osteoporosis), or undesirable conditions (e.g., pregnancy) can also be prevented, attenuated, or inhibited by appropriate in vivo administration of Ajoene.

Example 9

Ajoene Inhibits HIV Replication by Modulating Integrin-mediated Outside-in Signaling LAV-BRU 1 strain of HIV-1 and RF strain of HIV-1 were propagated in CEM and H9 cells, respectively. A 20-ml log-phase culture containing $7 \times 10^5$ cells per ml was incubated at 37° C. for 24 h. Cultures with less than 10% Trypan blue stained cells were used as a source of virus. To harvest HIV particles, producer cells were pelleted by centrifugation (400 g, 5 min) and the supernatant containing HIV-1 particles was filtered through a 0.45 micrometer Millipore filter, aliquoted, and stored at −80° C. The titer of HIV-1 ranged from $1 \times 10^5$ to $2 \times 10^5$ $CCID_{50}$ (50% cell culture infective dose). To determine whether Ajoene could influence HIV replication, CEM13 and H9 cells were inoculated with appropriate amounts of HIV (IAV-BRU 1 and RF, respectively), to give an m.o.i. (multiplicity of infection) of 0.1 in either experimental setting. Ajoene (or its vehicle) was added to $10^7$ infected cells resuspended in the growth medium and the cells were plated in 96-well flat-bottomed plates. After 72 h the bulk of HIV antigens was measured by solid phase immunoassay as described in Zhdanov, V. M., et al., An Enzyme Immunoassay for Detection of the Antigen and Antibody to the Human Immunodeficiency Virus and the Use Thereof For Serological Survey of Different Population Groups, 33 Vop. Virusol. 294, 1988 (in Russian). In a series of separate experiments Ajoene was introduced into plated cell cultures stepwise, i.e. in aliquots of 50 nanomoles per liter concentration per 12 h of incubation, the first addition coinciding with the moment of inoculation.

Replication of HIV-$1_{RF}$ in H9 cells was inhibited with an $IC_{50}$ of 25 micromoles per liter (m.o.i. 0.1; 72 h of incubation). Assessment of HIV-$1_{LAV-BRU\ 1}$ replication in CEM13 cells under the same experimental conditions revealed a more pronounced antiviral activity ($IC_{50}$ of about 5 micromoles per liter concentration). A considerable increase in the antiviral activity became evident when the concentration of the compound was increased stepwise (50 nanomoles per liter concentration per 12 h of incubation; CEM13 - LAV-BRU 1 system; inhibition by 30%; total concentration 0.25 micromoles per liter; m.o.i. 0.1; 72 h of incubation).

This example demonstrates that Ajoene affects the outside-in signaling function of integrins, thereby preventing the replication of HIV. The replication of HIV and of other viruses involves, as an essential step, the use of host cell protein-synthesizing machinery, which is regulated by integrin-elicited signals. Modulation of the outside-in signaling via integrins is, therefore, a way to control viral genes and the synthesis of viral proteins by the infected cells. Thus, administration of Ajoene to patients with viral infections can block the production of viral material and prevent the spread of viruses in the infected individual.

Furthermore, other cellular functions, not related to viral infection, can also be controlled by Ajoene, as this example demonstrates. These cellular functions include, without limitation, cell division, cell differentiation, and cell metabolic activity, such as production of mediators and enzymes. In the case of shock, for example, the synthesis of TNF depends on the outside-in signaling function of LFA-1 and can be prevented by appropriate modulation of this integrin (see, Watanabe, S., et al., Prevention of Endotoxin Shock by an Antibody against Leukocyte Integrin $\beta 2$ through Inhibiting Production and Action of TNF, 7 Int. Immunol. 1037, 1995; Mukaida, N., et al., Novel Insight into Molecular Mechanism of Endotoxin Shock: Biochemical Analysis of LPS Receptor Signaling in a Cell-Free System Targeting NF-κB and Regulation of Cytokine Production/Action through $\beta 2$ Integrin in Vivo, 59 J. Leuk. Biol. 145, 1996.). In a similar way, modulation of integrins and of their outside-in signaling function blocks the production of metalloproteinases, enzymes necessary for the invasion of trophoblasts (Loke, Y. W., et al., Adhesion Molecules and Trophoblastic Invasion, 23 Contracept. Fertil. Sex 573, 1995). Thus, this example provides further evidence of the efficacy of Ajoene against a wide range of diseases and undesirable conditions.

Example 10

Ability Of Ajoene To Protect Cells From Infection With Free Viruses and Virus-associated Pathologies The effect of Ajoene in protecting against HIV infection was evaluated using polymerase chain reaction (PCR) analysis which recognized amplified DNA sequences of HIV gag gene. MT-4 cells were used as target cells and strain IIIB of HIV-1 was used as inoculate. Serial dilutions of Ajoene or an equivalent volume of its vehicle were added to MT-4 cells, followed by addition of a sufficient amount of free virus ($\geq 10^3$ particles per cell). The protective effect of Ajoene was monitored by examining for the absence or presence of proviral HIV DNA in target cells 16 hours after the inoculation. Ajoene completely prevented HIV infection at the minimal dose of 4 mg/ml (17 micromoles per liter) and had an $IC_{50}$ of 5 micromoles per liter, without any toxic effects on the cells.

The effect on herpes simplex virus (HSV) infection was assessed using human embryonic lung fibroblast line WI-38 and HSV-2 strain G (derived from a human with the genital infection). Semiconfluent fibroblast monolayers grown in 96-well culture plates ($10^5$ cells per well) were exposed to serial dilutions of Ajoene or vehicle control, followed immediately by addition of HSV-2 (5000 $CCID_{50}$ per well). After 24 hours of culturing, the supernatants were examined by ELISA for the content of HSV antigens. Ajoene completely prevented HSV infection at 4 mg/ml (17 micromoles per liter) and had an $IC_{50}$ of 6 micromoles per liter, again, with no detectable toxicity.

This example provides evidence of Ajoene efficacy against the transmission of viral infections by free viruses. This mode may play a role in the transmission of the viruses both from infected individuals to uninfected individuals and from infected to intact cells. Thus, Ajoene can prevent both the entry of various viruses into the human body and the spread of viral infections within the infected individual's body.

In addition, as this example indicates, Ajoene can be used as an effective agent blocking sexual transmission of HIV and HSV. In addition, the entry of other microorganisms known to use the same portal to invade the human body will likewise be prevented. A preferred mode of administration of Ajoene in this use is, therefore, topical.

This example also demonstrates that Ajoene can prevent infections induced by Herpesviridae (e g., Epstein-Barr virus, cytomegaly virus, and other transforming herpesviruses). Ajoene, therefore, can protect from tumors induced by these viruses, as well as from diseases associated with herpetic infection (e.g., atherosclerosis), both in humans and animals.

Example 11

Ability of Ajoene to Prevent CD4-independent Cell-to-cell Transmission of HIV It has been shown that adhesion mediated by identified integrins (e g., VIA-4) is a critical step in the infection of human placental trophoblasts with HIV which is borne either by lymphocytes or by cells of lymphocytic cell lines. Experiments were, therefore, performed to ascertain whether the lymphocyte-to-trophoblast transmission of HIV can be inhibited by agents modulating the functional competence of the mediating integrins.

Human fetal placental epithelial cells, known as syncytiotrophoblasts, were organized in a monolayer and exposed to HIV-infected lymphocytic cells and, as a negative control, to uninfected cells of the same type. This experimental system, closely simulating the actual conditions under which syncytiotrophoblasts would be exposed to HIV-infected cells in vivo, was used to assess integrin-modulating effects of Ajoene.

MOLT-4 clone 8 cells were labeled with calcein-AM, pretreated with different concentrations of Ajoene (0–200 micromoles per liter) and incubated with cultured term syncytiotrophoblast cells at 37° C. for one hour in the presence of Ajoene. Adhesion was measured directly as fluorescence units after background correction. Controls included measuring adhesion in the presence of the appropriate carrier solvent. Without any toxic effects on cells, Ajoene inhibited adhesion of control MOLT-4 cells (not infected with HIV) to syncytiotrophoblasts with an $IC_{50}$ of 60 micromoles per liter. At the highest concentration tested (200 micromoles per liter), the inhibition was 100%, still without toxic effects.

In order to assess the ability of Ajoene to inhibit lymphocyte-mediated HIV infection of syncytiotrophoblasts, HIV-$1_{LBi}$-infected MOLT-4 cells were added to adherent cultures of uninfected syncytiotrophoblasts in the presence and absence of Ajoene. Various additional control conditions were also established. First, some wells received filtered (0.45 micrometer) supernatant of cell-free HIV from infected cell cultures. Yet other negative controls included syncytiotrophoblasts cultured alone and syncytiotrophoblasts cultured with uninfected MOLT-4 cells. After 24 hours, the cocultures were washed to removed unbound lymphocytes, fixed, permeabilized, stained for viral core antigens (p24 and p55), and viewed under a fluorescence microscope.

When present in the incubation medium at a concentration of 200 micromoles per liter, Ajoene totally prevented lymphocyte-mediated infection of the syncytiotrophoblasts by HIV without toxic effects to the cells in virtually all colonies. Moreover, even in the rare instances where some fluorescence was detectable, the signal was quite weak, indicating that any infection present was negligible. Notably, in the control wells that received only cell-free HIV, infection of syncytiotrophoblast cells was also totally inhibited by Ajoene, without toxic effects, at 200 micromoles per liter and also at lower concentrations tested. Cell-free HIV infection of the syncytiotrophoblasts did occur, however, when Ajoene was absent.

This example demonstrates that Ajoene is equiactive against HIV infection transmitted by free and cell-borne viruses to CD4-negative cells, indicating that the beneficial effects of integrin modulators are not limited to a particular stage of the disease or host cell target. Furthermore, the data disclosed in this example provide further proof of the activity of Ajoene in preventing HIV infection, particularly under the conditions of sexual transmission and mother-to-fetus transmission.

Example 12

Ajoene as a Potent Anti-Shock Agent

Neutrophil aggregation within the lung microvasculature is known to be a key event in the development of adult respiratory distress syndrome (ARDS), the main cause of death in patients suffering shock. Also, administration of neutrophil-aggregating agents (such as TPA, complement anaphylotoxins or N-formyl-L-methionyl-L-leucyl-L-phenylalanine, calcium ionophore A23187, arachidonic acid, and platelet-activating factor) to laboratory animals results in the development of ARDS. Certain inhibitors of neutrophil aggregation, such as anti-integrin monoclonal antibodies, have been shown to prevent lethality in experimental shock (see, e.g., Vedder, N. B., et al., A Monoclonal Antibody to the Adherence-Promoting Leukocyte Glycoprotein, CD18, Reduces Organ Injury and Improves Survival from Hemorrhagic Shock and Resuscitation in Rabbits, 81 *J. Clin. Invest.* 939, 1988).

The antiaggregatory activity of Ajoene disclosed in Examples 1 and 4, supra, is sufficiently high to indicate that Ajoene will be effective both for the prevention and treatment of various shock states (and related pathologies, such as ischemia-reperfusion injury and allograft rejection) by suppressing such aggregation.

Example 13

Ability Of Ajoene To Inhibit Fertilization

The activity of Ajoene in the hamster oocyte penetration assay was tested. This assay is routinely used to test the ability of capacitated human sperm to penetrate oocytes.

To obtain oocytes, mature hamsters (on day 1 of the estrous cycle) were injected intraperitoneally with 40 International Units (IU) pregnant mare serum gonadotropin (PMSG), followed by 40 IU human chorionic gonadotropin (HCG) 55 hours late. After 16 hours, the animals were sacrificed by intracardiac injection of 0.1 ml T61 (euthanizing agent), the oviducts were removed, and the cumulus mass was collected. Cumulus cells were removed by hyaluronidase treatment, and the freed oocytes were transferred into a watchglass containing 3 ml Biggers-Whitter-Whittingham (BWW) medium supplemented with human serum albumin (HSA) (BWW/HSA; pH 7.5). *Zona pellucida* was removed by trypsinization for 45 seconds, after which the thus-obtained zona-free oocytes were washed three times in BWW/HSA and finally resuspended in the same medium, with appropriate additions (as described below).

Human sperm was from a donor with known fertility (No. 113). The sample (freshly taken) was allowed to liquefy, was diluted 3:1 with BWW/HSA, was centrifuged at 325×g for 5 minutes, and was washed once with the same medium. A small portion of the original sample was analyzed (computer-assisted sperm analysis) using the Cell-Soft package. The pellet of washed sperm cells was subjected to the swim-up procedure (1 ml of the medium was added for this purpose). The swim-up was collected (about 0.5 ml), the cells were counted (Makler chamber), and their motility determined (%). The volume of the sample was adjusted with the medium to give $10^7$ cells per ml, and the samples were incubated overnight (18 hours) at 37° C. for capacitation. Thereafter, motility and cell density were determined once again, and the sample was divided into three equal portions, each to be subjected to appropriate treatment.

Ajoene (as a solution in ethanol) was added to separate suspensions of zona-free oocytes and capacitated sperm cells to give a final concentration of 200 micromoles per 1 (the final concentration of alcohol did not exceed 0.5%). Equivalent volumes of ethanol and BWW/HSA were added to the two control portions of each cell type (vehicle control and untreated cells, respectively).

After 30 minutes of separate incubation (37° C.) as per protocol above, sperm cells and oocytes subjected to the same treatment were brought into contact in 6-well culture plates, and the plates were transferred to an air incubator for an additional 3 hours (37° C.). Insemination was stopped by transferring oocytes from each well onto watchglasses, where the eggs were allowed to settle and were freed from excess sperm. Thereafter, slide-coverslip preparations were prepared from the contents of each watchglass and viewed under a phase-contrast microscope (x 40). Penetration was calculated by relating the number of penetrated oocytes to the total number of oocytes (values expressed as percentages).

Both intact and vehicle-pretreated gametes showed a high level of penetration (96.2% and 100%, respectively). Conversely, pretreatment with Ajoene inhibited penetration completely (0%).

It should be emphasized that the effect of Ajoene was not associated with toxicity or impaired cellular vitality (judging by intact motility of ajoene-pretreated sperm cells). All results were reliably reproduced (coefficient of variation did not exceed 15%).

In vivo, in humans and other mammals, sperm cannot penetrate or fertilize oocytes without first becoming capacitated. Capacitation ordinarily occurs in the genital tract of the human female. Once the species-specific zona pellucida has been removed from a hamster oocyte, however, the ability of capacitated human sperm to penetrate the zona-free hamster oocyte becomes a precise simulation of the in vivo ability of the same capacitated sperm to penetrate a human oocyte, as in the case of fertilization. It is, therefore, highly likely that Ajoene would exhibit the same activity in in vivo use as seen in this in vitro assay.

This example underscores once again the ability of Ajoene to modulate the adhesion and fusion function of integrins, and it also provides further proof that diseases and conditions associated with undesirable fusion can be prevented and treated with integrin modulators.

Example 14

Ajoene as an Antimetastatic Agent

Experimental Metastasis

A suspension of $10^5$ melanoma B16 cells was pretreated for 30 min with Ajoene, and the suspension (including Ajoene) was injected intravenously into male C57BL/6 mice. The mice were sacrificed 3 weeks post-injection, and their lungs subjected to microscopic examination. Ajoene prevented lung colonization at 200 micromoles per liter.

Melanoma Cell Implantation

Male C57BL/6 mice were inoculated subcutaneously with $10^6$ B16 cells (pretreated for 15 min with Ajoene) in their pretreatment medium, and the volume of the tumors formed was measured 14 and 21 days after the injection. Implantation was inhibited with an $IC_{50}$ of 2.5 micromoles per liter.

Example 15

Ajoene and Disintegrins Suppress Fusion Leading to Syncytium Formation in HTLV-I-infected Cells MT-2 cells harbor the complete genome of human T cell lymphotropic virus type 1 (HTLV-I), and they transmit the virus to susceptible uninfected cells in cocultures. The transmission manifests itself as fusion of MT-2 cells with the uninfected cells, followed by syncytium formation. K562 cells transfected with VCAM-1, a ligand of the integrin VIA-4, were used as a fusion partner for MT-2 cells. MT-2 and K562/VCAM-1 cells were washed and resuspended in complete RPMI medium at a density of $2\times10^6$/ml. MT2 cells were seeded into flat-bottom 96-well microtiter plates (100 microliters per well). Serial dilutions of Ajoene or of the disintegrin kistrin (final concentration) were introduced into the wells, and the plate was incubated for 30 min prior to addition of 100 microliters of K562/VCAM-1 cells. The plates were then incubated for 4 h before scoring syncytium formation.

Ajoene inhibited syncytium formation with an $IC_{50}$ of ~0.6 micromoles per liter and an $IC_{100}$ of 4.3 micromoles per liter. Kistrin inhibited syncytium formation by ~40% at 3.4 micromoles per liter; higher concentrations were not tested.

This example provides conclusive proof that the ability of Ajoene to prevent virus transmission cell-to-cell is not limited to HIV infection. Therefore, infections that are caused by other cell-borne viruses will likewise be inhibited by Ajoene in vivo. Thus, Ajoene can be used to prevent or treat a wide variety of viral infections in humans and animals.

Furthermore, when viewed in conjunction with the data of Examples 8 and 13, the result obtained herein indicates that Ajoene and like substances can prevent or attenuate adhesion and fusion events associated with a wide variety of conditions, diseases, and illnesses, whether induced by viruses, associated with inflammatory processes, or physiological.

Of equal importance, this example demonstrates that kistrin, a disintegrin modulating $\beta1$, $\beta2$, and $\beta3$ integrins, inhibits HTLV-I-mediated cell fusion.

Example 16

In Vivo Modulation by Disintegrins of LFA-1-and VLA-4-mediated Recruitment of Leukocytes in Murine Models of Human Autoimmune Diseases Nonobese diabetic (NOD) mice are characterized by spontaneous development of insulitis (similar to human insulin-dependent diabetes) and sialoadenitis (similar to Sjögren's disease). The development of autoirmune inflammation in these animals involves several integrin receptors, including VLA-4, CR3, and LFA-1 (CD11a/CD18). Lymphocyte infiltration into the pancreata is mediated primarily by VIA-4, whereas the predominant mechanism of lymphocyte recruitment into the salivary glands involves LFA-1.

NOD mice (age, 3 to 4 weeks old; average body weight, 10 g) were divided into three groups. Experimental animals received intraperitoneal injections of disintegrins (0.3 mg/kg per animal every other day) for 9 weeks. Control mice were administered with the vehicle.

The mice were sacrificed and subjected to autopsy. The pancreata and salivary glands were removed and frozen (−70° C.). Thin sections (5 micrometer thick) of these organs were fixed in acetone, stained with hematoxylin and eosin, and evaluated microscopically for lymphocyte infiltration (Tables 6 and 7).

TABLE 6

Effects of disintegrins on the spontaneous development of autoimmune diabetes

| Treatment | Number of mice vith infiltration scores: | | | |
|---|---|---|---|---|
| | − | + | ++ | +++ |
| Control | 0 | 1 (12.5%) | 3 (37.5%) | 4 (50%) |
| Eristostatin | 1 (20%) | 4 (80%) | 0 | 0 |
| Kistrin | 3 (60%) | 2 (40%) | 0 | 0 |

Infiltration score: (−) no infiltrating lymphocytes; (+) 1–3 infiltrated islets; (++) 4 islets with moderate infiltration and/or 1–2 islets with large infiltrates; (+++) 3 or more large infiltrates.

TABLE 7

Effects of disintegrins on the spontaneous development of autoimmune sialoadenitis

| Treatment | Number of mice vith infiltration scores: | | | |
|---|---|---|---|---|
| | − | + | ++ | +++ |
| Control | 1 (14.3%) | 2 (28.6%) | 3 (42.9%) | 1 (14.3%) |
| Eristostatin | 0 | 2 (40.0%) | 3 (60.0%) | 0 |
| Kistrin | 2 (40.0%) | 2 (40.0%) | 0 | 1 (20.0%) |

Infiltration score: (−) no infiltrating lymphocytes; (+) 1–3 small foci involving only one duct; (++) small foci and/or 1 large focus involving several ducts; (+++) 2 or more foci involving several ducts.

Eristostatin and kistrin increased the proportion of animals with mild infiltration of pancreatic islets and completely prevented the development of large infiltrates (lack of high scores; see, Table 6). Kistrin tended to be more active in this respect, judging from the higher percentage of animals with complete absence of infiltration. Similar effect was observed in the case of sialoadenitis (Table 7).

This example demonstrates that the recruitment of leukocytes to the tissues and the resulting development of autoimmune inflammation is dramatically retarded by modulation of $\beta1$ and $\beta2$ integrins with disintegrins. Thus, a broad range of autoimmune diseases (e.g., diabetes, Sjögren's syndrome, lupus, and rheumatoid arthritis) can be treated by modulators of $\beta1$ and $\beta2$ integrins.

Moreover, other types of destructive inflammation known to arise from excessive integrin-mediated recruitment of leukocytes (e.g., shock, ischemia-reperfusion injury, and graft rejection) will likewise be amenable to treatment with disintegrins.

Data disclosed in this example and Example 15, supra, indicate that disintegrins offer an approach to treatment of viral diseases, particularly in cases where the transmission of the virus occurs predominantly cell-to-cell and/or involves cell fusion. Other conditions, diseases, and illnesses, associated with excessive or otherwise undesirable cell fusion can, therefore, be treated by disintegrins with beneficial effects. Thus, disintegrins can be used as pharmaceuticals in various contexts, including, without limitation, the fields of infectious diseases, autoimmune diseases, shock and resuscitation from shock, transplantation (prevention of allograft rejection and GVHD), and reproductive biology.

Taken together, the examples clearly indicate that Ajoene modulates several integrins belonging to $\beta1$, $\beta2$, $\beta3$, and $\alpha4$ families of integrins. Notably, the modulating effects measured in vitro, such as inhibition of neutrophil aggregation (Example 1) and lymphocyte adhesion (Examples 4 and 5), are reproduced under in vivo conditions. As Examples 6 and 7 demonstrate, several inflammatory responses are significantly attenuated as a result of in vivo integrin modulation by Ajoene. Similarly, inhibition of VLA-4-dependent melanoma cell adhesion, observed in vitro (Example 3), takes place in vivo as well, judging by the suppression of melanoma metastasis (Example 14). The ability of Ajoene to modulate in vivo $\beta1$, $\beta2$, $\beta3$, and $\alpha4$ integrins strongly indicates that it can be used as a therapeutic agent in various contexts. Thus, Ajoene can be used in a range of clinical situations; it can be used to treat diseases, the pathogenesis of which is strongly integrin-dependent (e.g., HIV infection, shock, and inflammatory/autoimmune pathologies) and diseases and illnesses in which only certain stages or manifestations exhibit a dependence on integrin function. In addition, Ajoene can be used in the treatment of diseases with unknown etiology if these diseases involve an integrin-mediated aspect, such as inflammation. In this latter use Ajoene will mitigate the symptoms of the disease and alleviate the condition of the patients.

Furthermore, as demonstrated in Example 16 above, in vivo modulation of $\beta1$, $\beta2$, $\beta3$, and $\alpha4$ integrins by disintegrins produces the same therapeutic benefits as those described above for Ajoene. Thus, the same diseases, conditions and illnesses that Ajoene can treat are also treatable by disintegrins. In general, any non-antibody substance herein defined as a modulator of several integrin receptors (e.g., of a $\beta2$ integrin, such as LFA-1, and of $\beta1$ or $\alpha4$ integrin, such as VLA-4) will exhibit the same range of activities in vitro and in vivo as Ajoene and certain disintegrins (e.g., kistrin or eristostatin).

In the context of the pronounced homologies among various members of the integrin superfamily, the ability of Ajoene and disintegrins to act on integrins of distinct subfamilies clearly indicates that other integrins, not mentioned in the above Examples, can likewise be modulated with Ajoene and disintegrins to produce yet further therapeutic benefits. Therefore, the scope of this invention goes beyond specific pathologies involving $\beta1$, $\beta2$, $\beta3$, and $\alpha4$ integrins.

In order to achieve maximum benefit in treating a particular disease with modulators like Ajoene and disintegrins (which modulators act on several integrin receptors), it may be reasonable to use various targeted modes of administration. Methods of targeting pharmaceutical agents (and other substances) to desired locations, such as specific cells or organs, are well known in the art and described in numerous publications. One such method involves loading an integrin modulator into liposomes that contain on their surface antibodies against certain tissue markers, although other targeting techniques (including other targeting techniques based on antibodies) can also be used.

The above description has been offered for illustrative purposes only and is not intended to limit the scope of the invention of this application, which is as described in the claims below.

We claim:

1. A method of treating inflammation comprising administering to an animal suffering from inflammation an amount of an agent which is an integrin modulator effective to attenuate the inflammation.

2. The method of claim 1 wherein the inflammation is chronic.

3. The method of claim 2 wherein the chronic inflammation is caused by a chronic infection.

4. The method of claim 3 wherein the chronic infection is tuberculosis.

5. The method of claim 4 wherein the agent is administered by inhalation.

6. The method of claim 2 wherein the chronic inflammation is associated with sarcoidosis.

7. The method of claim 1 wherein the inflammation is acute.

8. The method of claim 1 wherein the inflammation is phlebitis, peritonitis or meningitis.

9. The method of claim 1 wherein the inflammation is associated with ischemia reperfusion injury.

10. The method of claim 1 wherein the inflammation is associated with an immune response.

11. The method of any one of claims 1–10 wherein the agent is a disintegrin, or a variant or analog thereof.

12. The method of any one of claims 2–10 wherein the agent is ajoene.

13. The method of any one of claims 1–10 wherein the agent is a non-antibody integrin modulating agent.

14. The method of claim 13 wherein the agent is a small non-antibody integrin modulating agent which is not an oligopeptide fragment of an integrin ligand or a cyclic derivative of such a fragment.

* * * * *